United States Patent
Star et al.

(10) Patent No.: US 11,712,200 B2
(45) Date of Patent: Aug. 1, 2023

(54) NANOSTRUCTURE-BASED CANNABINOID SENSOR

(71) Applicant: University of Pittsburgh—Of the Commonwealth System of Higher Education, Pittsburgh, PA (US)

(72) Inventors: Alexander Star, Pittsburgh, PA (US); Sean Hwang, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 572 days.

(21) Appl. No.: 16/608,096

(22) PCT Filed: Apr. 26, 2018

(86) PCT No.: PCT/US2018/029543
§ 371 (c)(1),
(2) Date: Oct. 24, 2019

(87) PCT Pub. No.: WO2018/200794
PCT Pub. Date: Nov. 1, 2018

(65) Prior Publication Data
US 2020/0093429 A1    Mar. 26, 2020

Related U.S. Application Data

(60) Provisional application No. 62/491,502, filed on Apr. 28, 2017.

(51) Int. Cl.
*A61B 5/08* (2006.01)
*A61B 5/00* (2006.01)
(Continued)

(52) U.S. Cl.
CPC ............ *A61B 5/4845* (2013.01); *A61B 5/082* (2013.01); *A61B 5/097* (2013.01); *A61B 5/1455* (2013.01); *A61B 5/1477* (2013.01); *C01B 32/159* (2017.08); *C01B 32/198* (2017.08); *G01N 33/948* (2013.01); *A61B 2562/0285* (2013.01)

(58) Field of Classification Search
CPC .. A61B 5/00; A61B 5/08; A61B 5/097; A61B 5/1455; A61B 5/1477; A61B 5/082;
(Continued)

(56) References Cited

U.S. PATENT DOCUMENTS 7,544,324 B2   6/2009   Tung
7,749,772 B1   7/2010   Wang
(Continued)

FOREIGN PATENT DOCUMENTS

WO      2018200794 A1    11/2018

OTHER PUBLICATIONS

Lu, Ganhua et al., Reduced graphene oxide for room-temperature gas sensors; Nanotechnology 20(2009), 445502, 1-9.

*Primary Examiner* — Eric J Messersmith
(74) *Attorney, Agent, or Firm* — Bartony & Associates, LLC

(57) ABSTRACT

A device for detection of tetrahydrocannabinol or THC in a sample includes a sensor including a substrate and a sensor medium on the substrate. The sensor medium includes at least one nanostructure, wherein at least one property of the sensor medium is dependent upon the presence of THC on a surface of the sensor medium. The device further includes electronic circuitry including at least one measurement system in operative connection with the sensor to measure a variable relatable to the at least one property of the sensor medium dependent upon the presence of THC.

23 Claims, 23 Drawing Sheets

(51) Int. Cl.
*C01B 32/159* (2017.01)
*C01B 32/198* (2017.01)
*A61B 5/097* (2006.01)
*A61B 5/1455* (2006.01)
*A61B 5/1477* (2006.01)
*G01N 33/94* (2006.01)

(58) Field of Classification Search
CPC ....... A61B 5/4845; A61B 5/7225; A61B 5/05;
A61B 2562/0285; A61B 2560/0204;
C01B 32/159; C01B 32/198; G01N
33/94; G01N 27/127; G01N 33/948;
G01N 2033/4975; B82Y 30/00; B82Y
15/00
See application file for complete search history.

(56) References Cited

U.S. PATENT DOCUMENTS

| | | |
|---|---|---|
| 7,790,400 B2 | 9/2010 | Jehanli |
| 8,237,118 B2 | 8/2012 | Prox |
| 8,920,764 B2 | 12/2014 | Star |
| 9,360,398 B2 | 6/2016 | Gold |
| 9,414,813 B2 | 8/2016 | Engel |
| 9,482,638 B2 | 11/2016 | Star |
| 2009/0017555 A1 | 1/2009 | Jehanli |
| 2010/0089772 A1* | 4/2010 | Deshusses ........... G01N 27/127 977/773 |
| 2010/0282245 A1* | 11/2010 | Star .................... G01N 33/0037 128/200.14 |
| 2011/0098591 A1* | 4/2011 | Haick .................... B82Y 15/00 977/788 |
| 2011/0217763 A1 | 9/2011 | Rasooly |
| 2013/0128260 A1* | 5/2013 | Palmskog ................. F01D 1/08 356/301 |
| 2015/0305651 A1* | 10/2015 | Attariwala ........... A61B 5/4845 600/532 |
| 2015/0369830 A1 | 12/2015 | Crichlow |
| 2016/0154015 A1 | 6/2016 | Stitzlein |
| 2016/0161459 A1* | 6/2016 | Rouse ..................... G01N 1/28 73/31.07 |
| 2016/0334387 A1 | 11/2016 | Ahmad |

* cited by examiner

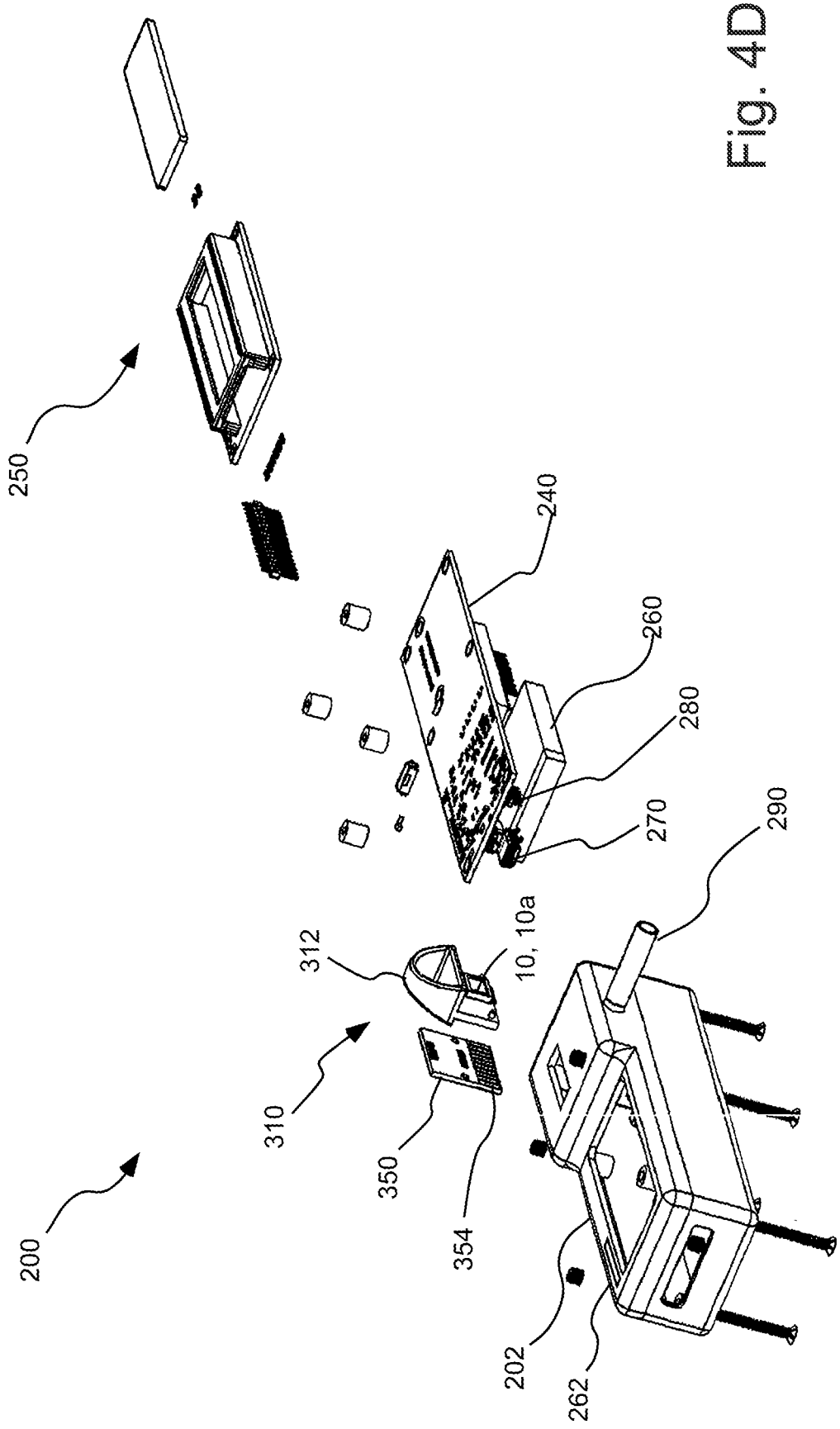

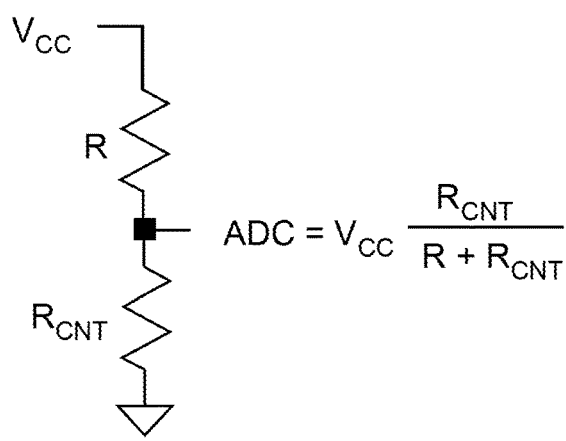
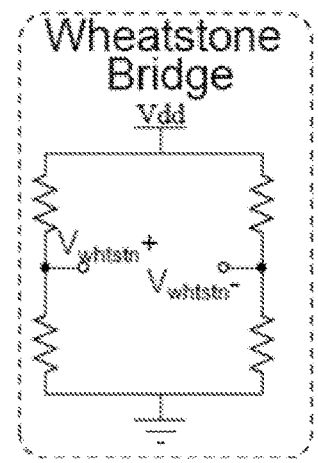
Fig. 4E
Fig. 4F
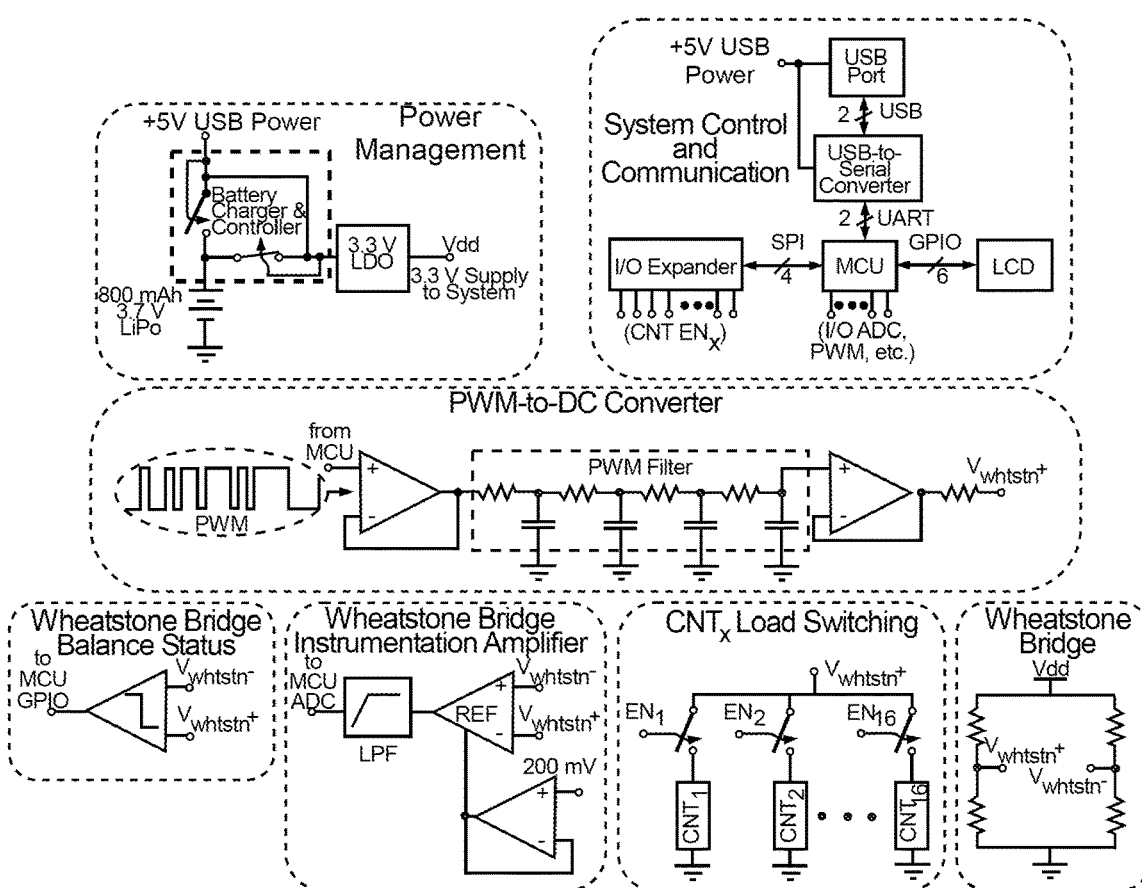
Fig. 4G

Raw Image

False Colored Image

NANOSTRUCTURE-BASED CANNABINOID SENSOR

CROSS-REFERENCE TO RELATED APPLICATIONS

This application is a national phase filing of PCT International Patent Application No. PCT/US2018/029543, filed Apr. 26, 2018, which claims benefit of U.S. Provisional Patent Application Ser. No. 62/491,502, filed Apr. 28, 2017, the disclosures of which i-s are incorporated herein by reference.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

The main isomer of tetrahydrocannabinol (THC), (−)-trans-$\Delta^9$-tetrahydrocannabinol, is the principal psychoactive constituent of cannabis or marijuana. In part, because marijuana is becoming legalized for both medical and recreational use in many parts of the United States, the law enforcement community requires a fast roadside method to test for THC intoxication in drivers. There are currently no suitable roadside methods that quantifiably measure marijuana intoxication. A number of THC breathalyzer technologies are based either on expensive and difficult to miniaturize mass spectrometry technology or on multistep automated processes that requires sample collection, release, and detection.

SUMMARY

In one aspect, a device for detection of tetrahydrocannabinol or THC (for example, in as gas phase or a liquid phase such as in breath or in a bodily fluid, respectively) includes a substrate and a sensor medium positioned on the substrate. The sensor medium includes at least one nanostructure. At least one property of the sensor medium is dependent upon or varies with the presence of THC on a surface of the sensor medium. Devices hereof may, for example, include a plurality of such sensors. The device further includes electronic circuitry including at least one measurement system in operative connection with the sensor or sensors to measure a variable relatable to (for example, a variable that varies with) variation in the at least one property of the sensor medium dependent upon the presence of THC. The variable may, for example, vary with varying concentration of THC such that a concentration of THC in the breath may be determined. The at least one property of the sensing medium dependent upon the presence of THC may, for example, be an electrical property or an optical property. In the case that the property is an electrical property, the measured variable may, for example, be conductance or resistance. The measurement system may, for example, include calibration information or data (for example, in the form of one or more threshold values, a lookup table, an algorithm or a formula) to determine a concentration of THC based upon a measured value of the variable. The device may, for example, further include a breathing tube into which breath may be exhaled, wherein an outlet of the breathing tube is in the vicinity of the sensor medium, The electronic circuitry may, for example, be operable, configured, or adapted to delay measurement of the property of the sensor medium affected by a change in the at least one property of the sensor medium for a period of time after application of a sample, (for example, breath) thereto. In a number of embodiments, the sensor is removable from the device. The sensor may, for example, be removed for replacement and/or to remove THC from a surface of the sensor medium (for example, via rinsing with a solvent). In a number of embodiments, the device includes a housing having a passage therein through which the sensor can be placed in operative connection with the electronic circuitry and removed from operative connection with the electronic circuitry.

In a number of embodiments, the sensor further includes a first conductive terminal in electrical connection with the sensing medium and a second conductive terminal in electrical connection with the sensing medium, wherein the second conductive terminal is spaced from the first conductive terminal. The sensor may, for example, operate as a chemiresistor or as a field effect transistor.

The nanostructure or nanostructures may, for example, include single-walled nanotubes, multiple-wall nanotubes, nanowires, nanofibers, nanorods, nanospheres, and nanoribbons. The nanostructure(s) may, for example, include or be formed from carbon, boron, boron nitride, carbon boron nitride, silicon, germanium, gallium nitride, zinc oxide, indium phosphide, molybdenum disulfide or silver. In a number of embodiments, the at least one nanostructure includes carbon nanostructures. In a number of embodiments, the nanostructure(s) include or are formed from carbon. In a number of embodiments, the nanostructure(s) include single-walled carbon nanotubes. In a number of embodiments, the nanostructure(s) include holey reduced graphene oxide.

The sensor medium may, for example, include a functional material deposited upon the nanostructures. The functional material may, for example, include at least one of a polymer (for example, a functional polymer), a surfactant, a biological moiety, a metal nanoparticle or a metal oxide nanoparticle. In general, the functional material is chosen to interact with THC to provide a response. In a number of embodiments, the sensor hereof includes nanostructures comprising carbon (for example, carbon nanotubes) functionalized with a THC specific functional material that changes in at least one electrical property (for example, conductivity or resistivity) when bound to or interacted with gas phase THC.

In a number of embodiments, the device includes a plurality of sensors, wherein each of the plurality of sensors includes a substrate and a sensor medium on the substrate, and the sensor medium includes at least one nanostructure. At least one property of the sensor medium is dependent upon the presence of THC on a surface of the sensor medium. In such embodiments, the at least one measurement system is in operative connection with each of the plurality of sensors to measure a variable relatable to the at least one property of the sensor medium which is dependent upon the presence of THC.

In another aspect, a method of detecting tetrahydrocannabinol or THC includes applying a sample to a sensor medium of a sensor or sensors. In a number of embodiments, detecting THC in breath includes having a person exhale such that exhaled breath contacts the sensor medium of a sensor or sensors. The sensor(s) may include a substrate upon which the sensor medium is positioned. As described above, the sensor medium includes at least one nanostructure, wherein at least one property of the sensor medium is dependent upon the presence of THC on a surface of the sensor medium. The method further includes measuring a variable relatable to the at least one property of the sensor medium which is dependent upon the presence of THC. The sensor(s) and sensing methodologies used in the methods hereof may be further characterized or described as set forth above.

In a further aspect, a sensor for detection of tetrahydrocannabinol or THC in a sample (for example, in breath or in a body fluid) includes a substrate and a sensor medium positioned on the substrate. The sensor medium includes at least one nanostructure. At least one property of the sensor medium is dependent upon or varies with the presence of THC on a surface of the sensor medium. The sensor may, for example, further include electronic circuitry including at least one measurement system in operative connection with the sensor medium to measure a variable relatable to the at least one property of the sensor medium which is dependent on the presence of THC. The sensor and its components or elements may be further characterized or described as set forth above.

The present devices, systems, and methods, along with the attributes and attendant advantages thereof, will best be appreciated and understood in view of the following detailed description taken in conjunction with the accompanying drawings.

BRIEF DESCRIPTION OF THE DRAWINGS

FIG. 4D illustrates a perspective, exploded view of the breathalyzer device or system of FIG. 4A.

FIG. 4E illustrates a simple voltage divider configuration of resistors, wherein a change in sensor resistance is converted to a change in voltage.

FIG. 4F illustrates a Wheatstone bridge configuration of resistors, wherein a change in sensor resistance is converted to a change in voltage.

FIG. 4G illustrates a schematic diagram of various components or portions of the device of FIG. 4A.

DETAILED DESCRIPTION

Figure 1A:
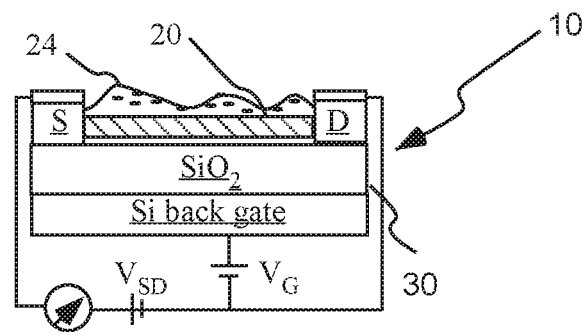
FIG. 1A illustrates schematically an embodiment of a THC sensor hereof which is operable as a field effect transistor or FET.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a nanostructure" includes a plurality of such nanostructures and equivalents thereof known to those skilled in the art, and so forth, and reference to "the nanostructure" is a reference to one or more such nanostructures and equivalents thereof known to those skilled in the art, and so forth. Likewise, reference to "a sensor" includes a plurality of such sensors and equivalents thereof known to those skilled in the art, and so forth, reference to "the sensor" is a reference to one or more such sensors and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

In general, nanostructures are structures of intermediate size between microscopic and molecular structures. Nanostructures may, for example, have at least one dimension in the range of 0.1 to hundreds of nanometers. Many nanostructures have at least one dimension in the range of 1 to 100 nm, Nanotubes are, for example, considered two-dimensional nanostructures and may have a diameter in the range of, for example, 0.1 nm to hundreds of nm and a length that may be significantly greater.

As used herein, the term "polymer" refers to a compound including a plurality of repeat or structural units. As known in the art, polymers can be formed via polymerization of one or multiple monomers. The term "oligomer" refers to polymers containing relatively few structural units The terms "electronic circuitry", "circuitry" or "circuit," as used herein include, but is not limited to, hardware, firmware, software or combinations of each to perform a function(s) or an action(s). For example, based on a desired feature or need. a circuit may include a software controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "control system" or "controller," as used herein includes, but is not limited to, any circuit or device that coordinates and controls the operation of, for example, one or more input or output devices. For example, a controller can include a device having one or more processors, microprocessors, or central processing units (CPUs) capable of being programmed to perform input or output functions.

The term "software," as used herein includes, but is not limited to, one or more computer readable or executable instructions that cause a computer or other electronic device to perform functions, actions, or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

In a number of embodiments, tetrahydrocannabinol (THC) sensors hereof include a sensing medium or material including bare or decorated/coated nanostructures (for example, single walled carbon nanotubes (SWCNTs)). In a number of embodiments, the sensors hereof may, for example, be deposited on microchips (for example, silicon-based microchips) with conductive (for example, metal such as lithographed gold) electrodes. The sensor hereof provide improved sensitivity, lower power consumption, and lower fabrication costs than currently available sensors for THC. A sensor chip hereof may, for example, be implemented into a handheld device to be used as a breathalyzer for measurement of the concentration of THC in breath samples. The gold standard for measuring and quantifying THC in body fluids is liquid chromatography-mass spectrometry, which involves a large benchtop instrument that requires chemical solvents, pumping systems, vacuum systems, and high powered electronics. Current roadside testing devices can measure THC only in saliva and sweat, which may not be accurate for THC intoxication and show high rates of false positives resulting from marijuana use many hours or even days previous to the test.

Chemically sensitive solid-state resistors (chemiresistors) and field effect transistors (FETs) hereof exhibit room temperature gas phase and/or liquid phase sensitivity to determine THC levels in, for example, a breathalyzer test or a saliva test hereof. In NTFET (nanotube field-effect transistor) devices, one, for example, measures electrical current through nanotubes such as carbon nanotubes under an applied gate voltage. In chemiresistor devices, a gate voltage is not applied. In both types of devices, an electrical property (for example, conductance or resistance) of nanostructures such as nanotubes changes upon exposure to chemical analytes, thereby providing a sensor signal. Depending on the semiconducting nature of the nanostructures, application of a gate voltage can provide amplification of the sensor signal. Nanotubes such as single-walled carbon nanotubes or SWCNTs provide an ideal candidate for incorporation into extremely small and low power devices because they demonstrate extreme environmental sensitivity, high electrical conductivity, and inherent compatibility with existing microelectronic fabrication techniques.

Figure 1B:
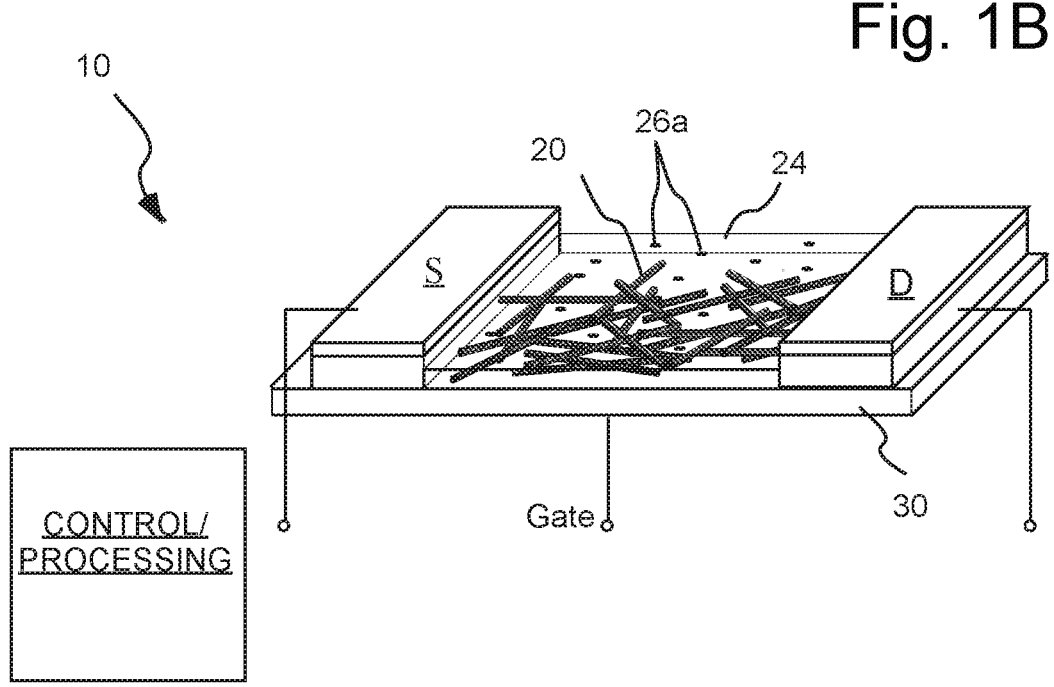
FIG. 1B illustrates a perspective schematic view of a portion of the sensor of FIG. 1A.
Figure 2:
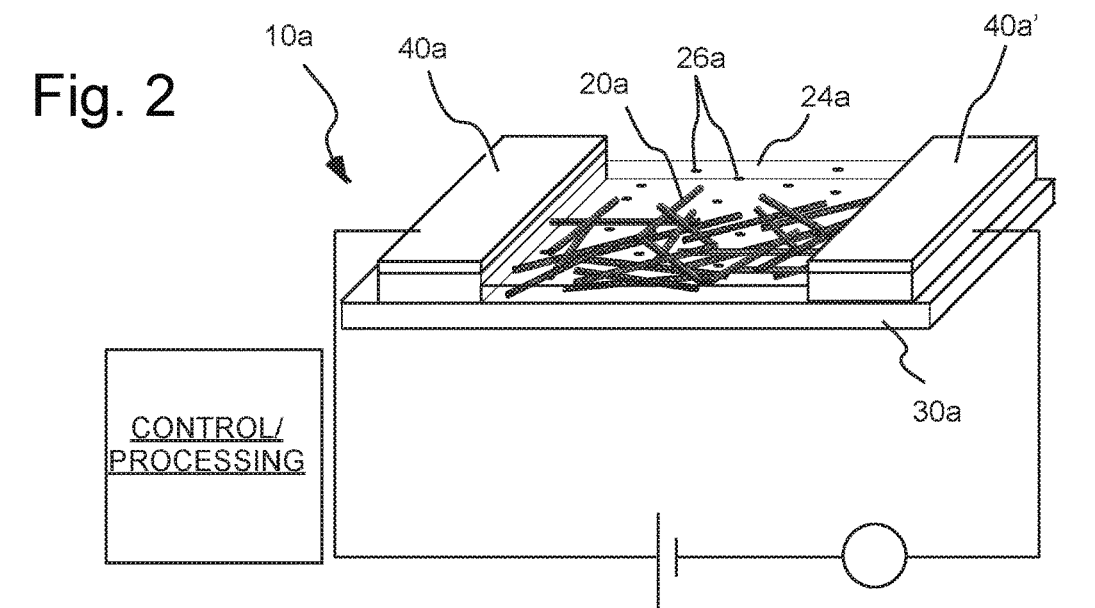
FIG. 2 illustrates a perspective schematic view of a THC sensor hereof which is operable as a chemiresistor.

A schematic representation of an NTFET sensor system 10 hereof is set forth in FIGS. 1A and 1B, while a chemiresistor sensor system 10a hereof is illustrated in FIG. 2. As described above, the illustrated sensor systems 10, 10a include a sensing medium material including one or more representative nanostructures including, for example, single-wall carbon nanotubes or SWCNTs 20, 20a (for example, a network of SWCNTs). Single walled carbon nanotubes classified based on their electrical properties. Nanotubes may, for example, be considered to be either semiconducting or metallic. Nanotube synthesis process typically yields mix of both metallic and semiconducting nanotubes. Purification steps are required to enrich the samples to be either mostly metallic or mostly semiconducting. Either mixed or purified nanostructures may be used in the sensor systems hereof.

As clear to those skilled in the art, various other nanostructures are suitable for use in the present invention. Such nanostructures include, but are not limited to, multiple-wall nanotubes, nanowires, nanofibers, nanorods, nanospheres, nanoribbons (for example, interconnected nanoribbons of holey reduced graphene oxide) or the like, or mixtures of such nanostructures. Moreover, in addition to carbon, those skilled in the art will appreciate that the nanostructures of the present invention can be formed of boron, boron nitride, and carbon boron nitride, silicon, germanium, gallium nitride, zinc oxide, indium phosphide, molybdenum disulfide, silver, and/or other suitable materials.

As illustrated in FIGS. 1A and 1B, the sensing medium or material, including semiconducting SWCNTs or a network of SWCNTs 20 (or other nanostructures), may, for example, be disposed upon a substrate 30 (for example, silicon dioxide or quartz) and contacted by two conductive (for example, metallic—such as Au and/or Ti) electrodes representing a source (S) (a conductive electrode or terminal) and a drain (D) (a conductive electrode or terminal). In the operation of an NTFET circuit such as illustrated in FIGS. 1A and 1B, changes in electrical conductivity may, for example, be measured for an applied gate voltage. One may, for example, measure current flow between source (S) and drain (D) as a function of a swept/varied gate voltage range. NTFET sensor hereof may, for example, be used in the gas phase or the liquid phase to sense THC. In the liquid phase, the sensing material may, for example, be covered in liquid phase. For example, certain biological or bioactive moieties (for example, receptors) may function better in a liquid phase.

As described above, a chemiresistor device such as device 10a need not include an applied gate voltage. In chemiresistor 10a the sensing medium or material, including nanostructures 20a, bridges the gap between two conductive electrodes 40a and 40a' (for example, gold electrodes), which may be referred to a source and a drain. The sensing medium or material may alternatively coat a set of interdigitated electrodes. The resistance/conductance between electrodes 40a and 40a' can be readily measured. The sensing medium or material has an inherent resistance/conductance that is changed by the presence of the analyte. In a chemiresistor, a source-drain bias voltage may, for example, be swept through a range of voltages, and drain current may be measured. Chemiresistor sensor hereof may, for example, be used in gas-phase detection of THC.

In a number of representative embodiments, the sensing media or materials hereof include one or more materials (or functional materials) deposited or decorated upon the nanostructures thereof. For example a layer 24, 24a of a polymeric material (for example, a conductive polymeric material) or a surfactant may be decorated on nanostructures 20, 20a. Additionally or alternatively, metal or metal oxide (for example, gold, palladium platinum, silver, titanium dioxide, zinc oxide, indium oxide, and tin oxide) nanoparticles 26, 26a of various size (for example, in the range of approximately 1-300 nm, 1-100 nm, or 10-50 nm) may be deposited. Materials designed to specifically interact with THC may also be used. For example, such materials may be biological materials. For example, certain proteins such as cannabinoid receptors and antibodies may be used. Aptamers, which are oligonucleotide or peptide molecules that bind to a specific target molecule, may also be used. Cannabinoid receptors and a number of antibodies are activated by cannabinoids. Functional materials may, for example, be deposited upon a sensing medium or material hereof via many processes including, for example, electrodeposition, EDC-NHS covalent coupling chemistry, sodium borohydride reduction of metal ions and sol-gel synthesis. In EDC-NHS coupling chemistry, NHS (N-hydroxysuccinimide) and sulfo-NHS may, for example, be used to prepare amino-reactive esters of carboxylate groups for crosslinking and immobilization. Carboxylates (including a —COOH group) may be reacted to NHS or sulfo-NHS in the presence of a carbodiimide (for example, EDC, (1-ethyl-3-[3-dimethylaminopropyl]carbodiimide)) to result in a NHS or sulfo-NHS ester, which may subsequently be reacted with primary amines (—NH$_2$) to form amide crosslinks.

In single-walled carbon nanotubes, all carbon atoms are located on the surface where current flows, making a stable conduction channel that is extremely sensitive to a surrounding chemical environment. Nanotubes, including single walled nanotubes (SWNTs) such as SWCNT's, have the ability to change conductance in response to interaction with (for example, absorption of) different gases. This characteristic is, for example, implemented in systems 10 and 10*a*. Once again, support 30, 30*a* may, for example, be an insulating layer of quartz or silicon dioxide in a FET-configured or chemiresistor circuit.

Measurements made with devices or systems including random networks of SWNTs can be advantageous because random network devices are less prone to failure as a result of the large number of conduction pathways. Additionally, while random network devices may not provide information on individual nanotube response, as with singly isolated SWNT systems, they possess an intrinsic averaging effect in that they remove nanotube-to-nanotube variation as a result of the combined response of the entire network. As an analyte comes into contact with the device surface, SWNT conductance is modified to produce a detection signal.

Figure 3A:
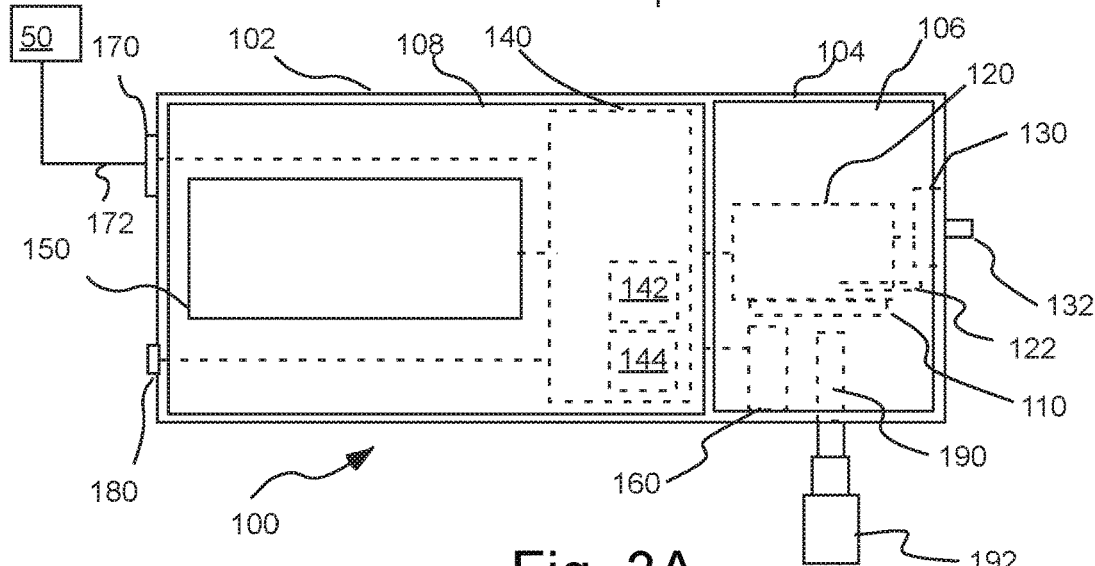
FIG. 3A illustrates schematically an embodiment of a breathalyzer device or system hereof including the sensor of FIG. 2 in a sensor assembly.
Figure 3B:
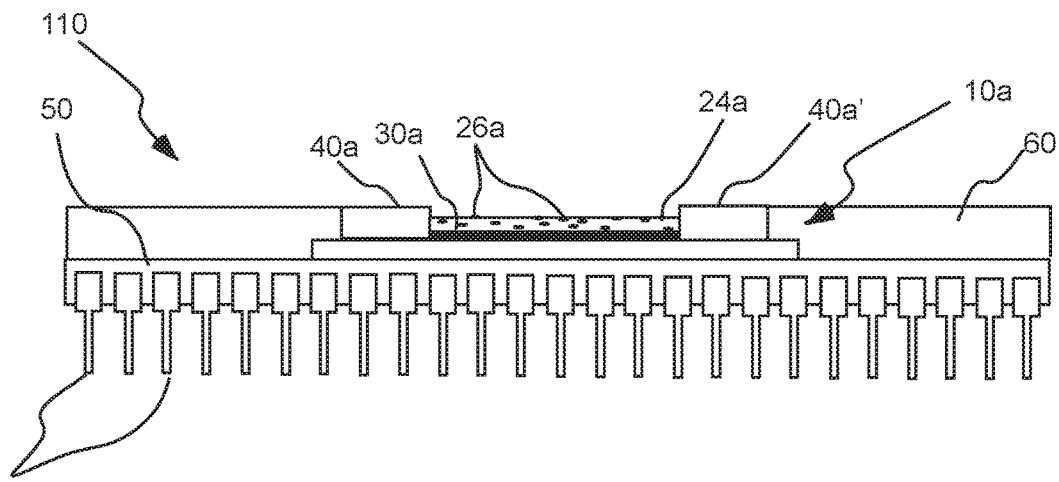
FIG. 3B illustrates the sensor assembly of FIG. 3A wherein a sensor of FIG. 2 is deposited upon a silicon-based microchip.
Figure 3C:
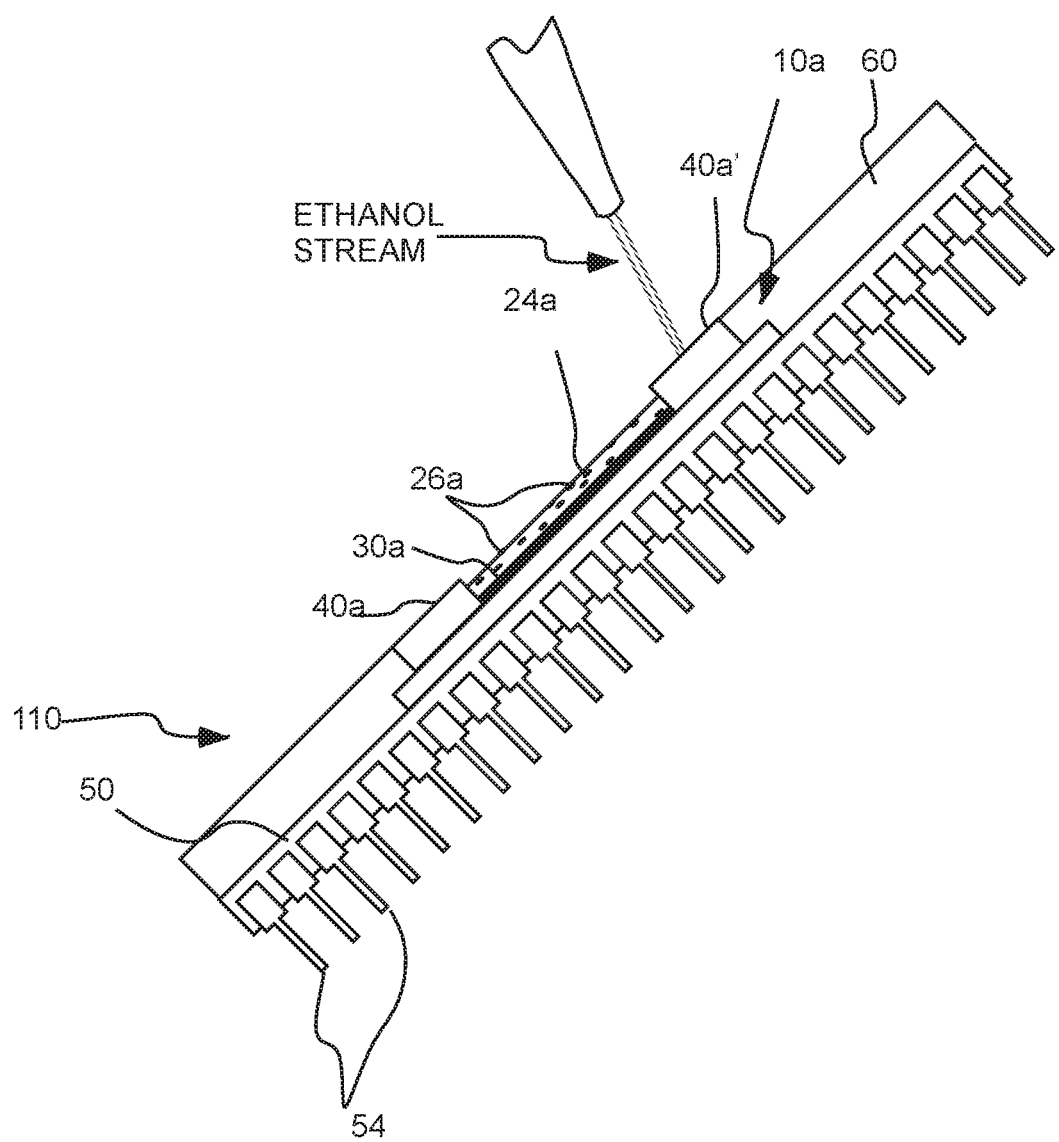
FIG. 3C illustrates a cleaning process or methodology for the sensor of the breathalyzer device or system of FIG. 3A.
Figure 3D:
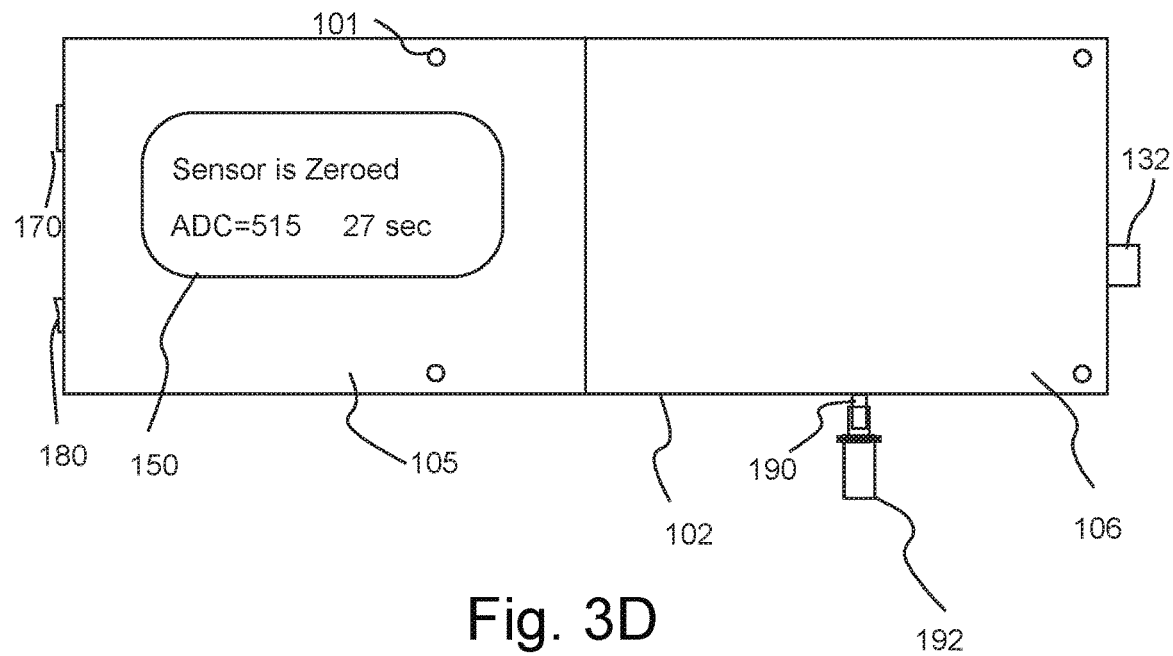
FIG. 3D illustrates schematically the breathalyzer device or system of FIG. 3A in a closed-panel state.
Figure 3E:
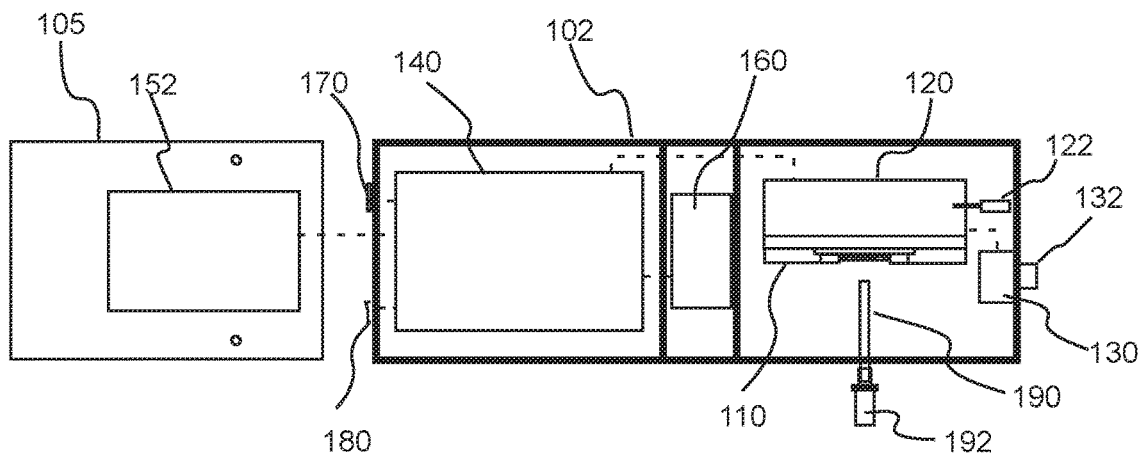
FIG. 3E illustrates schematically the breathalyzer device or system of FIG. 3A in an open-panel state.

As described above, one or more sensor systems or devices hereof may, for example, be deposited onto a microchip such as a silicon-base microchip. FIGS. 3A, 3D and 3E illustrate an embodiment of a prototype device or system 100 used in a number of studies hereof including a microchip-based sensor assembly 110 in which chemiresistor 10*a* is deposited on a silicon wafer 50 as illustrated in FIGS. 3B and 3C. Sensor assembly 110 is removably and operably attachable to a sensor assembly connector 120 within 100 via conductive connector pads 54 as known in the electronics and computer arts. An adjustment circuit, including, for example, a potentiometer 130 (which is adjustable via an adjustment control/knob 132 in the illustrated embodiment), may, for example, be provided in connection with sensor assembly 110 to zero out the sensor signal so that sensor sensitivity is maximized. Sensor assembly 110 is placed in connection with a control board 140 (for example, a printed circuit board or PCB) via connector 120. Control board 140 includes or has attached thereto a controller system or processor system 142 (including, for example, one or more microprocessors or microcontrollers) and a memory system 144 which is placed in operative or communication connection with the processor system via control board 140 or integrated with the processor system. Control board 140 is also in operative connection with a display 150 such as a liquid crystal display via a control board 152 (for example, a printed circuit board or PCB) therefor attached to a housing panel 105 (see FIG. 3E). A power supply/battery 160 such as a 9V battery may be supplied to power one or more electronic circuitry components as described above. Such electric circuitry components may be housed within a housing 102.

A USB or other communication port 170 in operative connection with control board 140 may extend through housing 102. An on/off or power switch 180 may, for example, be provided on housing 102. A breath tube 190 passes through housing 102 and has an outlet in the vicinity of chemiresistor 10*a* of sensor assembly 110. A mouth piece 192 may be provided at an inlet of breath tube 190.

In a number of embodiments, a USB cable 172 is connectible between USB port 170 and a computer 50 such as a general purpose personal computer or PC (see FIG. 3A). In initializing device 100, device 100 may, for example, be powered through USB port 170 without turning power switch 180 to the on position. Software or code for, for example, control and/or data transfer may be uploaded to breathalyzer 100 during an initialization process. In that regard, a continuous data acquisition code may send the sensor reading from an analog signal pin of control board 140, displays it to LCD display screen 150 and sends it to PC 50. In a number of embodiments, the displayed value is the analog signal from chemiresistor sensor 10*a* converted to bits. Once the code is uploaded and bit values are being displayed on LCD display screen 150, the user may turn the potentiometer knob 132 until the LCD display screen 150 displayed a value as close to as predetermined value (for example, 512) in a number of embodiments as possible. A value between 500 and 524 was acceptable in a number of embodiments. Once again, potentiometer knob may be used to zero out the sensor signal so that the sensitivity is maximized.

Once code is uploaded, USB cable 172 may be disconnected and device 100 may be turned on via power switch 180. In this mode, device 100 is, for example, powered by battery 160. In a number of embodiments, the code has four sequences: Zeroing, Baseline Reading, Breath Sampling, and Response Reading. In Zeroing, potentiometer knob 132 is adjusted until LCD display screen 150 displayed a value as close to, for example, 512 as possible, as described above. A timeframe of 60 seconds may, for example, be provided to zero out the sensor. The time may, for example, be adjusted by adjusting a "zeroing" variable. In the Baseline Reading sequence, a baseline signal from chemiresistor sensor 10*a* is measured over a period of, for example, 10 seconds. The signal should read close to, for example, 512, since chemiresistor sensor 10*a* should have been zeroed in the previous sequence. The baseline reading time may, for example, be changed by changing an "initialization" variable. In the breath sampling sequence, an individual blows into device 100 for the designated time (for example, 10 s). The breath sampling time may, for example, be changed by changing a "blow-time" variable. In the response reading sequence, device 100 waits for a designated time and then, for example, takes 100 sensor measurements in the last 10 seconds. The designated time may, for example, be changed by changing an "analysis-time" variable. In a number of embodiments, the wait time was 600 seconds. This time period was chosen because any breath humidity that condenses on chemiresistor sensor 10*a*, as well as other small-molecule cross contaminants such as ethanol of acetone, evaporate on this time scale, whereas the THC stays bound and does not evaporate. Heat or low pressure/vacuum may, for example, be applied to more quickly evaporate small-molecule cross contaminants such as ethanol, acetone and water that may be present in the breath of a person blowing into device 100.

Because THC does not desorb from the sensor surface within a reasonable timeframe under the conditions of testing, THC may, for example, be rinsed off the surface of chemiresistor sensor assembly 110 with a liquid suitable to extract the THC (for example, ethanol). In that regard, THC is a larger molecule with a relatively high molecular weight, which does not readily vaporize from the sensor surface. An embodiment of a sensor cleaning methodology is shown in FIG. 3C. In a number of embodiments, a user may disconnect a sensor panel 106 of breathalyzer 100 (for example, via connectors such as screws 101—see FIG. 3D) from the rest of housing 102 to access sensor assembly 110. The user then orients device 100 so that mouth piece 192 is pointing upwards. A connector lever 122 is then raised to release sensor assembly 110 from sensor assembly connector 120. After raising connector lever 122, one can pull out sensor assembly 110 as straight up and as gently as possible to prevent potentially bending sensor assembly connection pins 54 (which were gold in a number of embodiments)

and/or contacting sensor assembly 110 with breath tube 190. In a number of embodiments, a protective (for example, ceramic) top portion 60 was provided on sensor assembly 110. In the clearing process, one may hold sensor assembly 110 by ceramic top portion 60 and orient sensor assembly 110 in, for example, a range of angles from 45 degrees to nearly perpendicular (90 degrees) with respect to the direction of gravity. Care should be taken not to bend gold connection pins 54. In this position, on may gently flow, for example, an ethanol stream just above sensor 10a on sensor assembly 110 as illustrated in FIG. 3C. The ethanol stream will roll down and wash sensor 10a. One should avoid directly rinsing sensor 10a with the ethanol stream. Sensor assembly 110 may be dried at 60° C. for 10 minutes to dry off the ethanol. After drying, gold connection pins 54 may be aligned with cooperating connectors of sensor assembly connector 120. One may gently push sensor assembly 110 back into connection with sensor assembly connector 120. Excess force should be avoided to not damage/bend connection pins 54. After connection, one may gently push down connector lever 122. Sensor panel 106 may then be reattached. Battery 160 may be replaced by removal of a display panel 108 (via, for example, connectors such as screws).

Figure 4A:
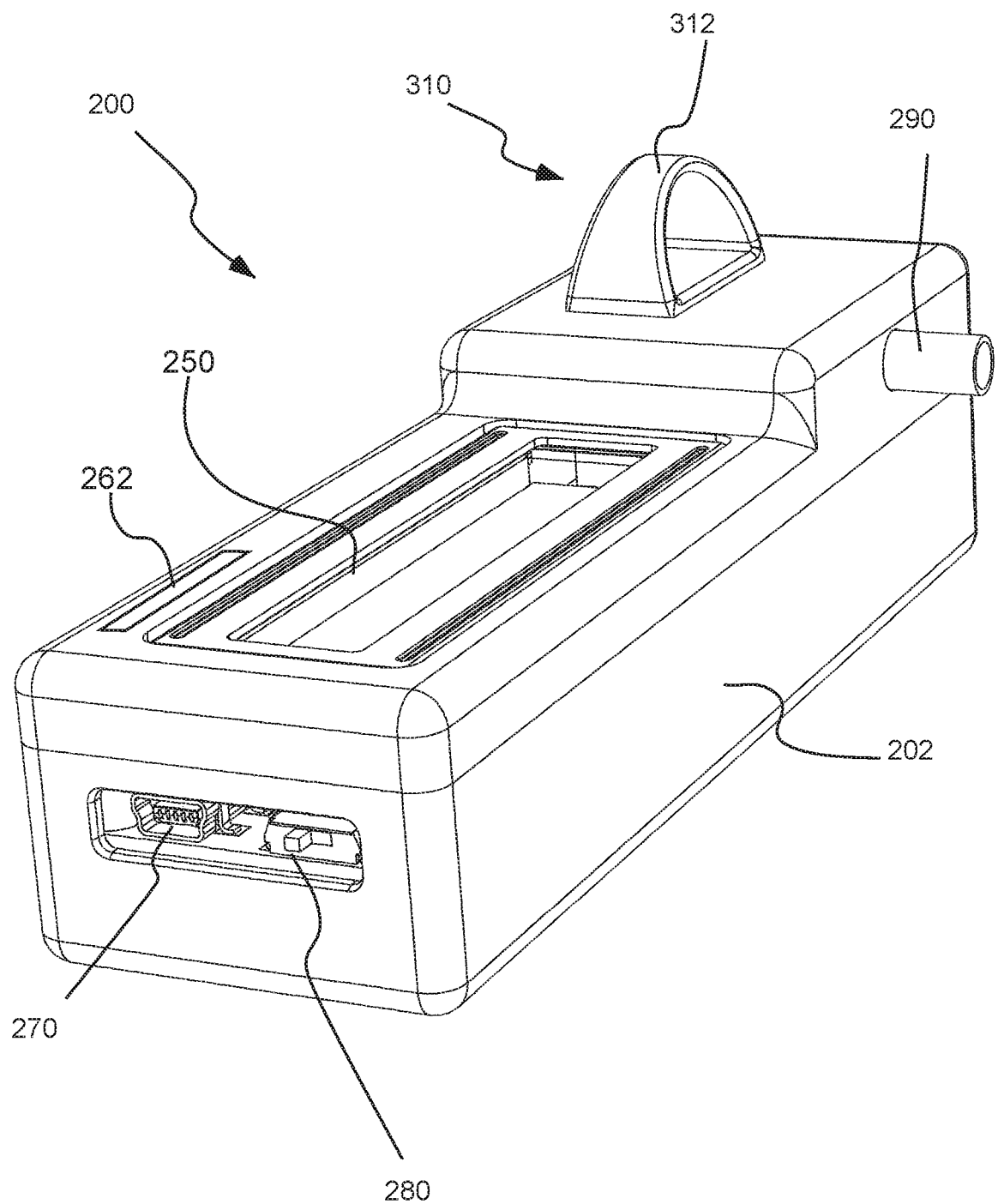
FIG. 4A illustrates a perspective view of another embodiment of a breathalyzer device or system hereof.
Figure 4B:
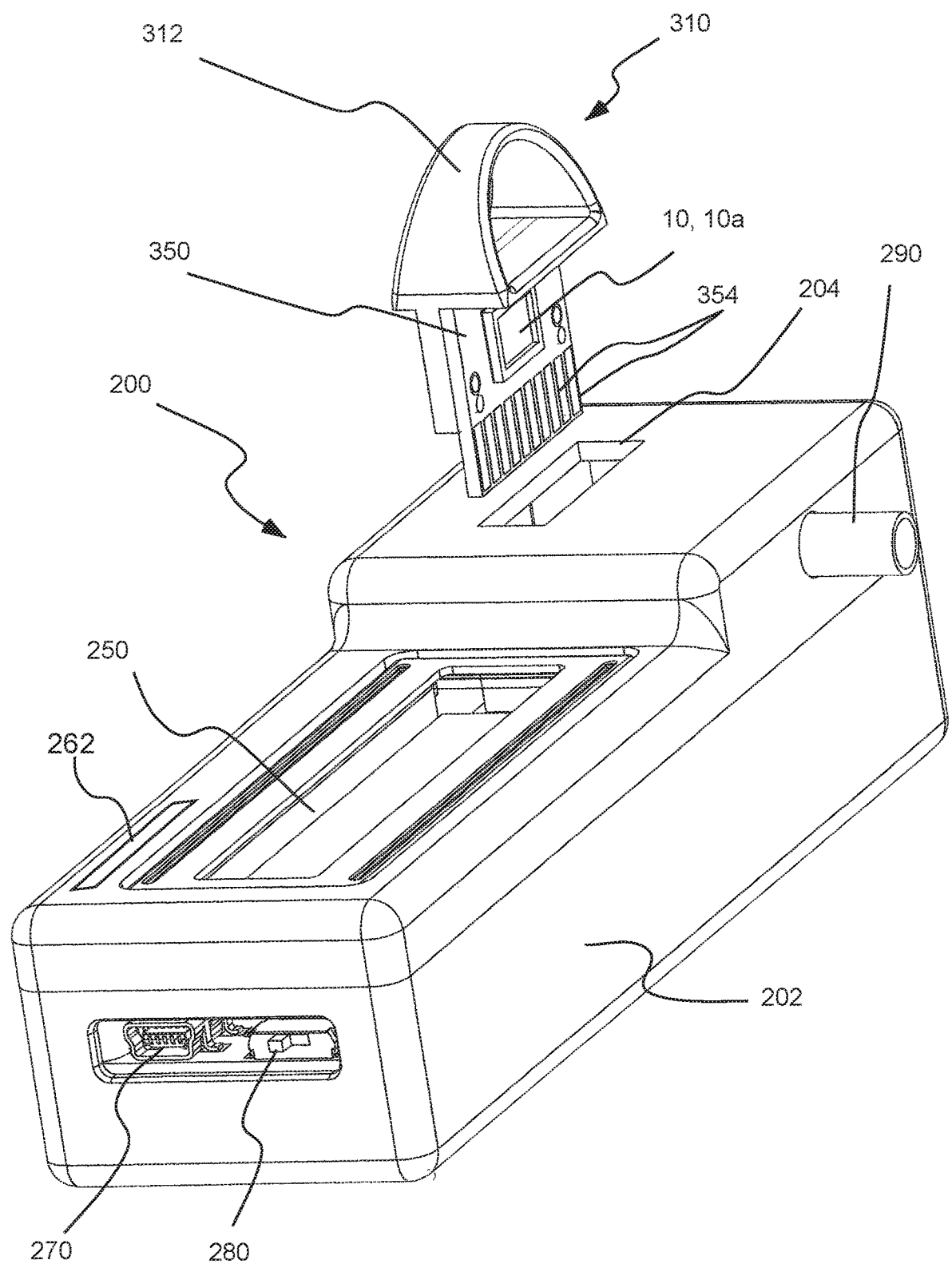
FIG. 4B illustrates a perspective view of the breathalyzer device or system of FIG. 4A wherein the sensor assembly is removed from connection with the device.
Figure 4C:
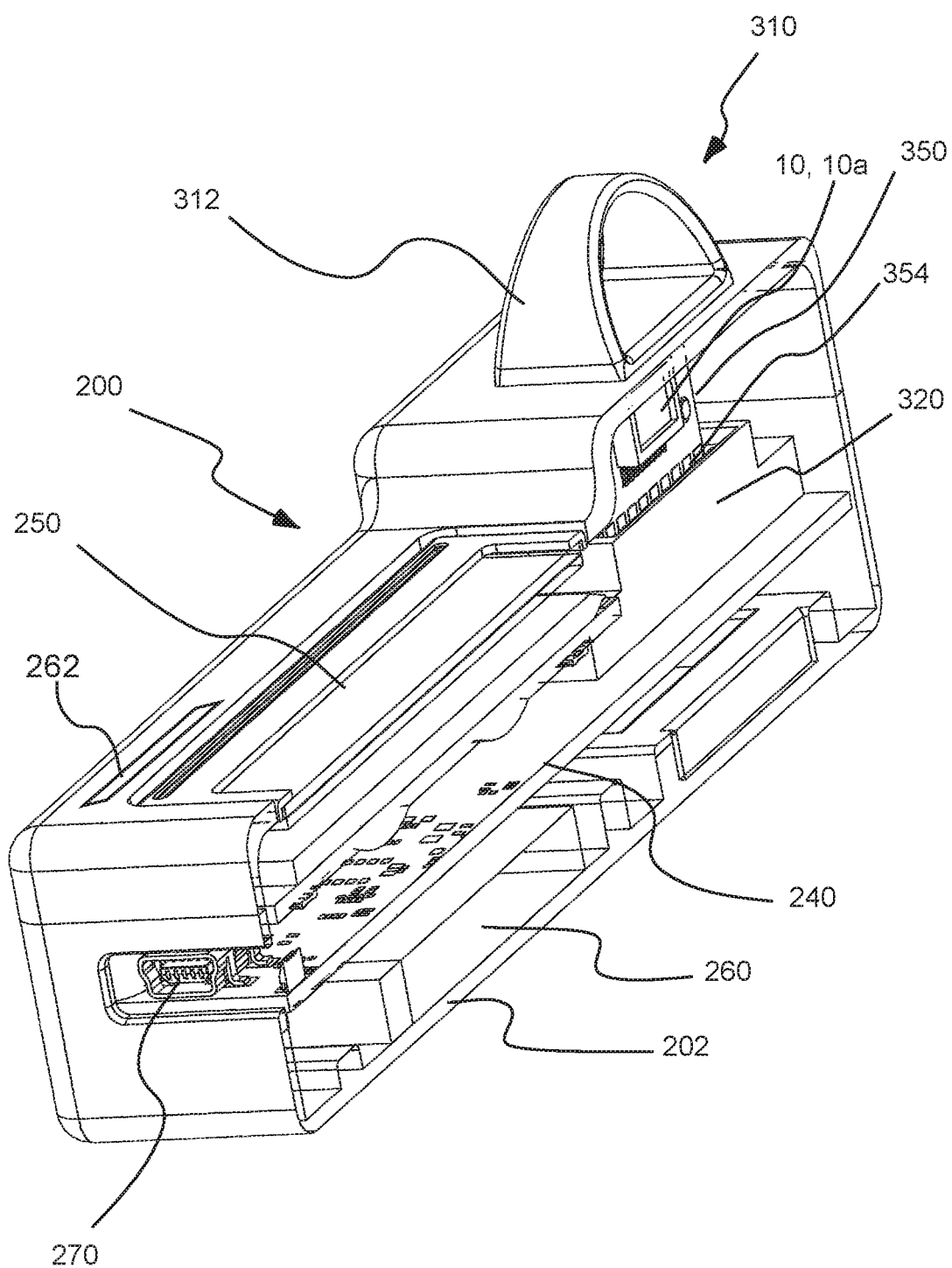
FIG. 4C illustrates a perspective, cutaway view of the breathalyzer device or system of FIG. 4A.

FIG. 4A through 4F illustrated another embodiment of a device or system 200 hereof for detection of THC in a more compact form than device or system 100. Similar to device 100, device 200 includes a microchip-based sensor assembly 310 in which one or more chemiresistors 10a or A FETs 10 is/are deposited on a silicon wafer 350 as illustrated in FIGS. 4B through 4D. Sensor assembly 310 is readily removably and operably attachable to a sensor assembly connector or receptacle 220 within breathalyzer housing 202 via a handle or gripping portion 312 on a first or outer end and conductive connectors 354 on a second or inner end. Sensor assembly 310 is placed in connection with a control board 240 (for example, a printed circuit board or PCB) via connector 220.

In the illustrated embodiment, sensor assembly 310 may be placed in and out of connection with connector or receptacle 220 via a slot or opening 204 formed in housing 202. The design of device 200 thereby facilitates removal of sensor assembly 310 for cleaning/replacement as compared to device 100. A user may, for example, be provided with multiple sensor assemblies 310 in a system of kit for use in connection with device 200. Sensor assemblies 310, when removed from connection with device 200, may, for example, be cleaned as described above or discarded.

Control board 240 includes or has attached thereto a controller system or processor system (not shown; including, for example, one or more microprocessors) and a memory system (not shown) which is placed in operative or communication connection with the processor system via control board 240 (as described in connection with control board 140) or integrated with the processor system. Control board 240 is also in operative connection with a display 250 such as a liquid crystal display. A power supply/battery 260 (for example, a Lithium Polymer or LiPo battery) may be supplied to power one or more electronic circuitry components as described above. Such electric circuitry components are housed within a housing 202.

A mini USB or other communication port 270 in operative connection with control board 240 may extend through housing 202. Mini USB or other communication port 270 may, for example, be used to connect to a PC to, for example, effect software revision and/or data transfer, to effect battery charging and/or to effect power the device (for example, even if battery 260 is absent or damaged). An indicator 262 (for example, one or more LED lights) may be provide to set forth information such as battery status. Status indicator(s) 262 may, for example, indicate when battery 260 is low (RED), when the device is charging battery 260 (BLUE), and when charging of battery 260 is complete (GREEN). An on/off or power switch 280 may, for example, be provided on housing 202. A breath tube 290 passes through housing 202 and has an outlet in the vicinity of chemiresistor 10a or FET 10 of sensor assembly 210. A mouth piece may be provided at an inlet of breath tube 290 as described above.

In a number of embodiments, beginning when a sensor assembly 310 is plugged into connector 320 of device 200, device 200 is powered or turned on. Screen display 250 (for example, a liquid crystal screen display or LCD) may, for example, show a message asking the user to blow into mouthpiece tube 290. Internally, device 200 performs several tasks before it reports whether THC is present in the user's breath. In the illustrated embodiment, the presence of THC changes the resistance of sensor 10, 10a, which is sensed by device 200. If a change in resistance greater than a threshold resistance (for example, 1% below the nominal sensor resistance) is sensed, then THC is determined to be present. In a number of representative embodiments, the nominal sensor resistance was expected to be at least 7.4 kΩ.

Methodologies for sensing changes in sensor resistance in device 200 are shown in FIGS. 4E and 4F. FIG. 4E illustrates a simple voltage divider configuration of resistors, where a change in resistance is converted to a change in voltage. In the voltage divider network, one resistor (R) is a fixed value, and the other resistance ($R_{CNT}$) is variable, wherein $R_{CNT}$ represents the sensor resistance. In a number of embodiments, an analog-to-digital converter (ADC) is the input port of a digitizing device, such as a microcontroller/microprocessor. Sensing changes in $R_{CNT}$ is easier when the resistance change results in a larger voltage change. The point where the largest voltage change occurs will be when R equals the nominal sensor resistance before a measurement is taken (for example, R=$R_{CNT}$).

In a number of embodiments, the resistor network in device 200 was a Wheatstone bridge, which uses the same principle of voltage division described above, but increases the resistance-sensing accuracy with a more complex resistor configuration as illustrated in FIG. 4F. Three of the resistor values are known. The fourth resistor value can be calculated from a measurement of the differential voltage between the centers of each "leg" of the bridge, labeled in FIG. 4F as $V_{whtstn}$. Sensor 10, 10a forms the bottom half of one leg of the bridge.

Once the device is powered or turned on, the Wheatstone bridge is balanced according to the nominal resistance of sensor 10, 10a. This balancing serves as a calibration step. Once the Wheatstone Bridge is balanced, a user breathes onto sensor 10, 10a. If THC is present in the user's breath, the sensor's resistance will change, causing the Wheatstone bridge to become unbalanced. The imbalance in the Wheatstone bridge will create a very small voltage (μV to mV) between the bridge legs, which may require amplification before it can be sensed by electronics. The amplified voltage is sent to a microcontroller unit (MCU) via an analog-to-digital converter (ADC). Software on the MCU determines whether there has been a change in voltage from the initial calibration, and the LCD screen is updated to indicate the presence/absence of THC.

FIG. 4G illustrates a schematic diagram of the components of device 200. Referring to FIG. 4G, The Power Management portion of the design converts either the +5V USB power (via mini-USB port 270) or the battery 260 (a 3.7V LiPo battery in several embodiments) to a regulated 3.3V for the entire device's electronic circuitry. A battery charger/controller handles recharging battery 260 and simultaneously powering the system when the +5V USB connection is made.

In a number of embodiment, the core of the System Control and Communication portion of the design is the CC1110 microcontroller unit or MCU available from Texas Instruments of Dallas, Tex. The MCU uses an I/O expander, via a 4-wire Serial Peripheral Interface (SPI) to enable each sensor (CNT in FIG. 4, in a representative embodiment of a carbon nanotube or CNT sensors) individually. The MCU also writes messages to LCD display 250. If the +5V USB connection is made, then the MCU can communicate with a computer host via USB through the USB-to-Serial Converter (FT232).

The PWM-to-DC Converter converts a Pulse-Width Modulation (PWM) signal output from the MCU to a direct current (DC) voltage. The conversion is accomplished through a filter network situated between two op-amp buffers.

The Wheatstone Bridge Instrumentation Amplifier, Wheatstone Bridge Balance Status, $CNT_x$ Load Switching, and Wheatstone Bridge portions are related and interconnected. The $CNT_x$ Load Switching portion is where a specific CNT sensor load is switched into use via the MCU programming the I/O expander. In a representative embodiment, up to seven sensors can be multiplexed. The Wheatstone Bridge uses four resistors as described above, wherein two sets of two resistors connected in series between the system supply voltage and ground. The voltage between the two series resistors in each of the two legs can be balanced by the PWM-to-DC Converter. The Wheatstone Bridge Balance Status activates when the Wheatstone Bridge has been balanced via the PWM-to-DC Converter. The Wheatstone Bridge Instrumentation Amplifier amplifies a difference between the two legs of the Wheatstone Bridge. In a number of embodiments, the Wheatstone Bridge and amplifier circuitry allows a nominal sensor resistance range of 7.4 k$\Omega$-2 M$\Omega$.

Figure 4H:
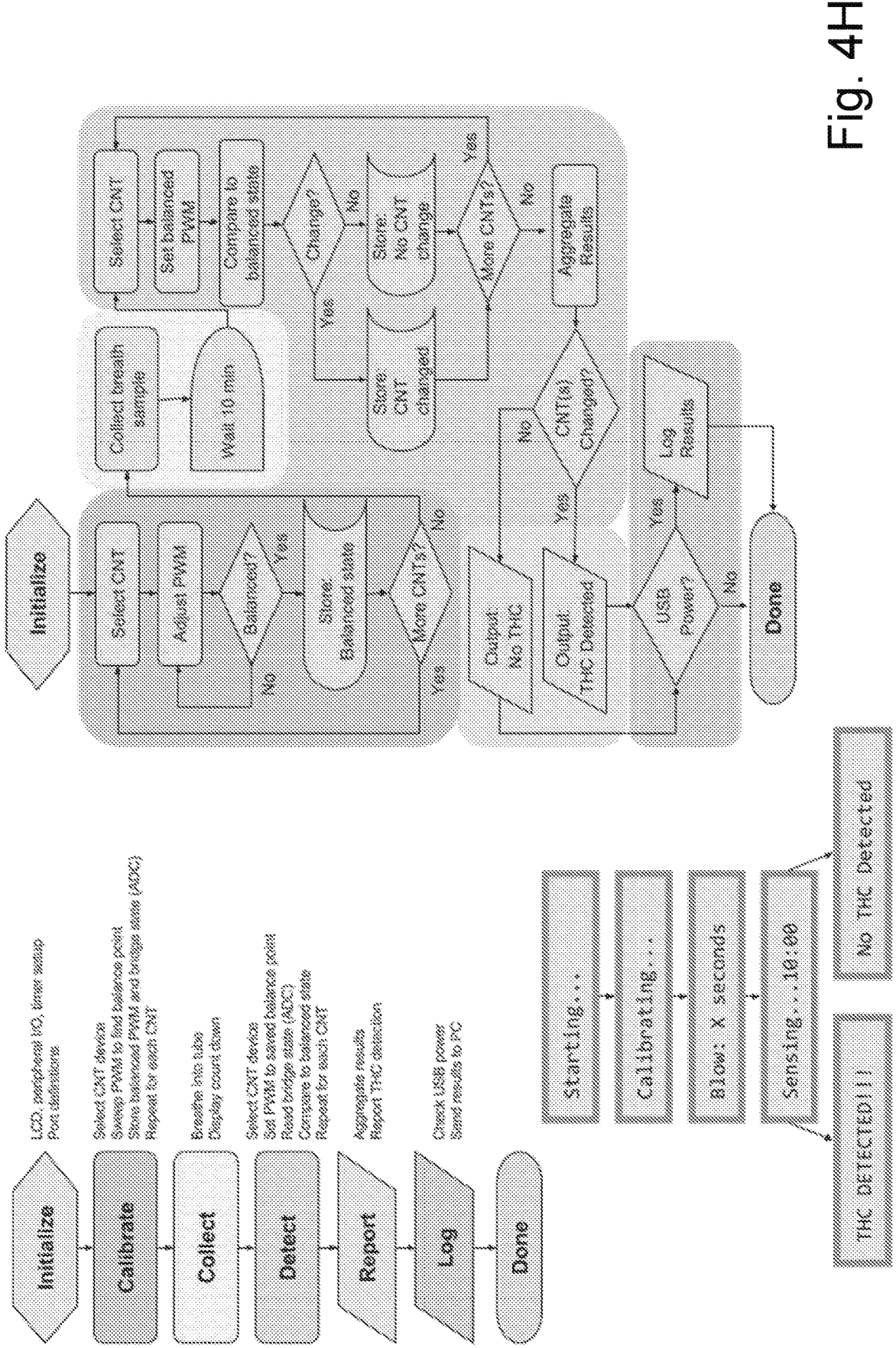
FIG. 4H illustrates embodiments of software flowcharts for the operation of the device of FIG. 4A and examples of display status messages associated with the software.

FIG. 4H illustrates embodiments of software flowcharts for the operation of device 200 and examples of display status messages. The sequence of operations is summarized in FIG. 4H as specified by software on the processor system/MCU as described above. When device 200 is powered on, there is an initialization step in which display and MCU functions and ports are set up. Following initialization, device 200 automatically calibrates by sweeping values of the PWM to find the balanced state of the Wheatstone bridge as described above. The value of the Wheatstone bridge differential voltage $V_{whtstn}$ is also stored for later comparisons, via the analog to digital converter or ADC. Multiple sensors 10,10a may be included in device 200 or other devices hereof. In a number of representative studied embodiments, the calibration may be performed for up to seven sensors 10, 10a, with the calibration state stored for each sensor 10, 10a. A number displayed on the display 250 while calibrating may, for example, correspond to various conductor pad 354 of sensor assembly 310. While calibrating, each sensor 10, 10a is powered (by applying 3.3 V to the Wheatstone bridge and connecting each sensor 10, 10a to one leg of the bridge), and then no voltage is applied across sensors 10, 10a during a wait time before checking sensors 10, 10a for a change in resistance. When checking for a change in resistance, each sensor 10, 10a is powered again. Because sensors 10, 10a are not powered during the wait time, this is a "Pulsed" powering scheme.

Following calibration, display 250 instructs the user to breathe into the tube for a predetermined or present COLLECTION_TIME seconds (in a number of embodiments, a predetermined default period of time was 5 seconds). The device then waits SENSE_WAIT_TIME seconds (in a number of embodiments, that period of time defaulted to 300 seconds, or 5 minutes) for the sensor/CNT to stabilize after collecting the breath sample.

Device 200 then cycles through sensors 10, 10a, setting the PWM to the calibration value corresponding to each sensor 10, 10a, and reading the state of the Wheatstone bridge via the ADC. The state is compared to the calibration value, and a difference from the calibration value of more than a variable ADC_THRESHOLD_1 indicates a change in the sensor resistance induced by the presence of THC. Whether there is a difference from the calibration value is stored for each sensor 10, 10a.

After determining/reading whether there has been a change in the resistance of each sensor 10, 10a, device 200 then aggregates the results, and outputs whether THC was detected to display 250. If, for example, 50% or more of the sensors that were calibrated changed from their initial resistance value, device 200 reports that THC was detected.

The operation of the device was verified using fixed resistors, connecting a resistor in parallel to simulate a 1% decrease in the resistance. As described above, device 200 detects a change in the sensor conductance/resistance by reading the voltage difference in the Wheatstone bridge, via the ADC. In a number of embodiments, the ADC had a resolution of 10 bits with 2's complement representation, allowing positive and negative values. For a number of studies, only a difference from the balanced value was determined, and therefore only the lower 9 bits of the ADC was used, allowing a total of 512 values. Typical ADC values for a 7.4 k-Ohm nominal resistance were a calibration ADC value of 0x011D=285, and a 1% change gave average values in the range [0x008F, 0x0099]=[143, 153] when averaging 100 values. A 1% change was confirmed detectable for resistances greater than or equal to 7.4 k-Ohms, with a theoretical maximum resistance of 2 M-Ohms.

In another embodiment, in a "continuous" powering scheme device 200 cycles through the pins on sensor assembly 310 while calibrating, and once one sensor 10, 10a is calibrated, that sensor 10, 10a remains powered through the wait time until it is checked for a change in resistance. Because the sensor is continuously powered during the wait time, this is referred to as a "continuous" powering scheme. However, because only sensor 10, 10a can be connected to the Wheatstone bridge at a time, only one sensor 10, 10a can be continuously powered through the wait time and used for sensing.

Another embodiment of an operation mode is similar to the pulsed mode described above, except that during the reporting stage, device 200 checks the difference between the calibration value and the current value against multiple thresholds. Therefore, it can report two concentration levels depending on how much the resistance has changed. The thresholds for determining which concentration are defined by the variables ADC_THRESHOLD_1 and ADC_THRESHOLD_2 as configuration values in the software. A change of greater than ADC_THRESHOLD_1 but less than ADC_THRESHOLD_2 is reported as a "Level 1" change, and a change of greater than ADC_THRESHOLD_2 is reported as a "Level 2" change.

Another embodiment of an operation mode is similar to the pulsed mode described above, except that during the reporting stage, device 200 checks the difference between the calibration value and the current value and reports a concentration level. The code can detect up to NUM_CONCENTRATIONS concentration levels, and the difference between each concentration level is defined by ADC_THRESHOLD. A change of ADC_THRESHOLD is reported as a "Level 1" change, a change of 2*ADC_THRESHOLD is reported as a "Level 2" change, a difference of 3*ADC_THRESHOLD is reported as a "Level 3" change, etc. up to NUM_CONCENTRATIONS levels.

Figure 5A:
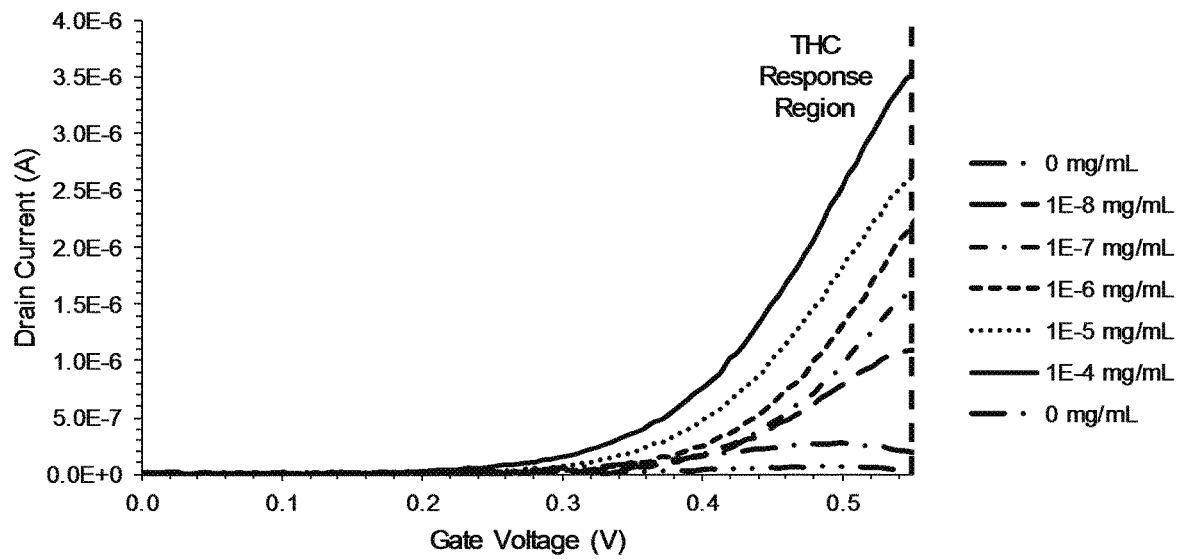
FIG. 5A illustrates the THC response at various concentrations of THC for a sensor include SWCNTs from Purus Nano of Bishan Green, Singapore.
Figure 5B:
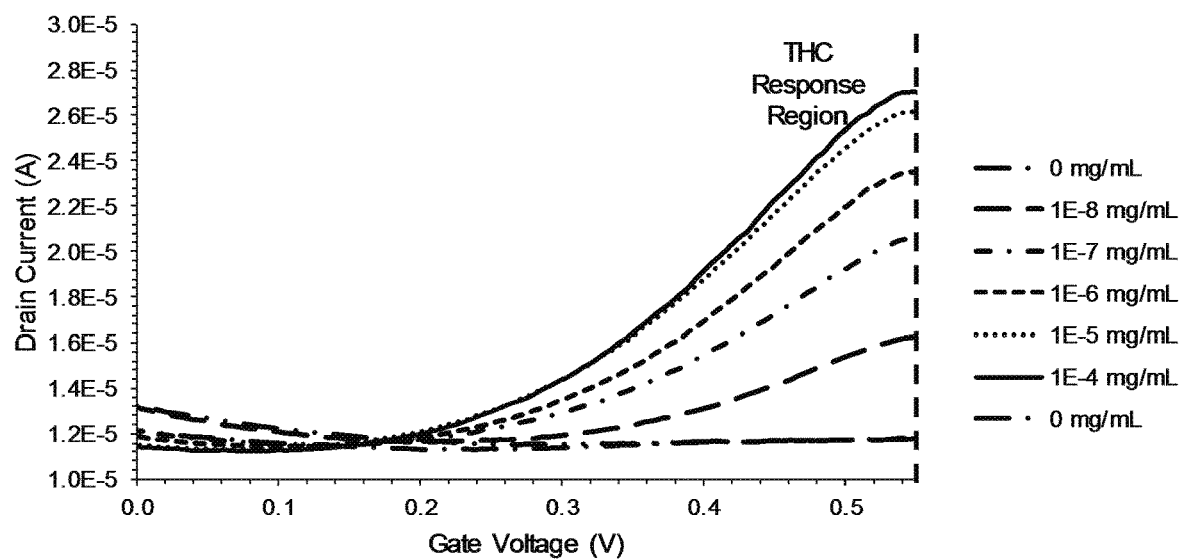
FIG. 5B illustrates the THC response at various concentrations of THC for a sensor including P2 SWCNTs available from Carbon Solutions, Inc. of Riverside, Calif. USA.
Figure 6A:
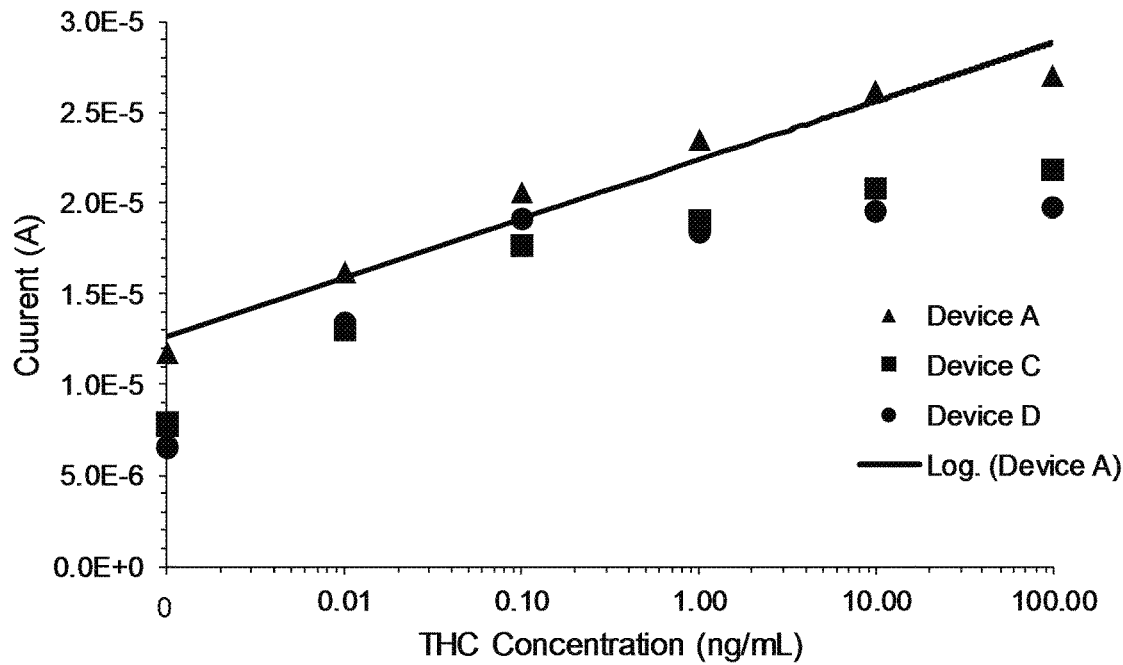
FIG. 6A illustrates that there is a logarithmic relationship between measured current and THC concentration at the relevant low concentrations for the Purus Nano SWCNT sensor of FIG. 5A.
Figure 6B:
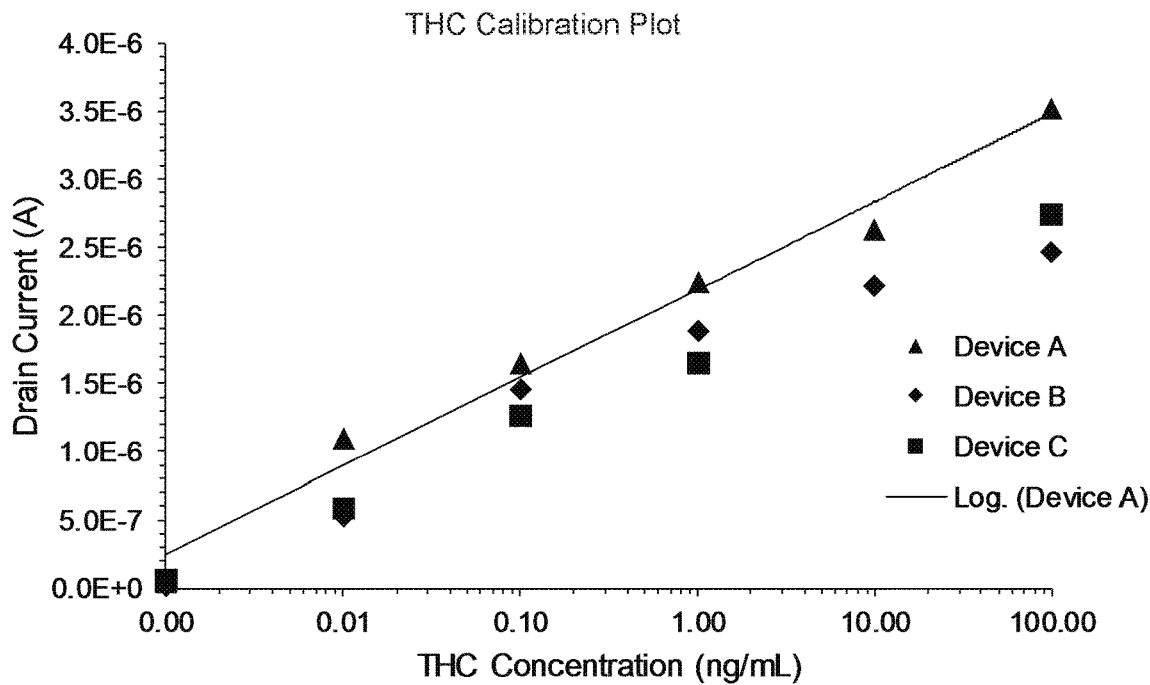
FIG. 6B illustrates that there is a logarithmic relationship between measured current and THC concentration at the relevant low concentrations for the P2 SWCNT sensor of FIG. 5B.

In a number of representative studies hereof, tetrahydrocannabinol (THC) NTFET sensors hereof included a sensing medium or material including bare or decorated/coated single walled carbon nanotubes (SWCNTs) deposited onto a silicon-based microchip with lithographed gold electrodes. When the sensing medium or material comes in to contact with THC dissolved in, for example, ethanol or in dried state, the conductivity of the SWCNTs changes proportionally to the concentration or the mass of the THC. The changes in electrical conductivity may, for example, be measured in liquid phase as measured current at 0.55 V applied gate voltage for the Purus Nano and P2 SWCNTs. FIGS. 5A and 5B, respectively, illustrates the THC response at various concentrations of THC for a Purus Nano SWCNT sensor and a P2 SWCNT sensor. FIGS. 6A and 6B, respectively, illustrate that there is a logarithmic relationship between the current and THC concentration at the relevant low concentrations for both the Purus Nano and P2 SWCNT sensors.

Figure 7A:
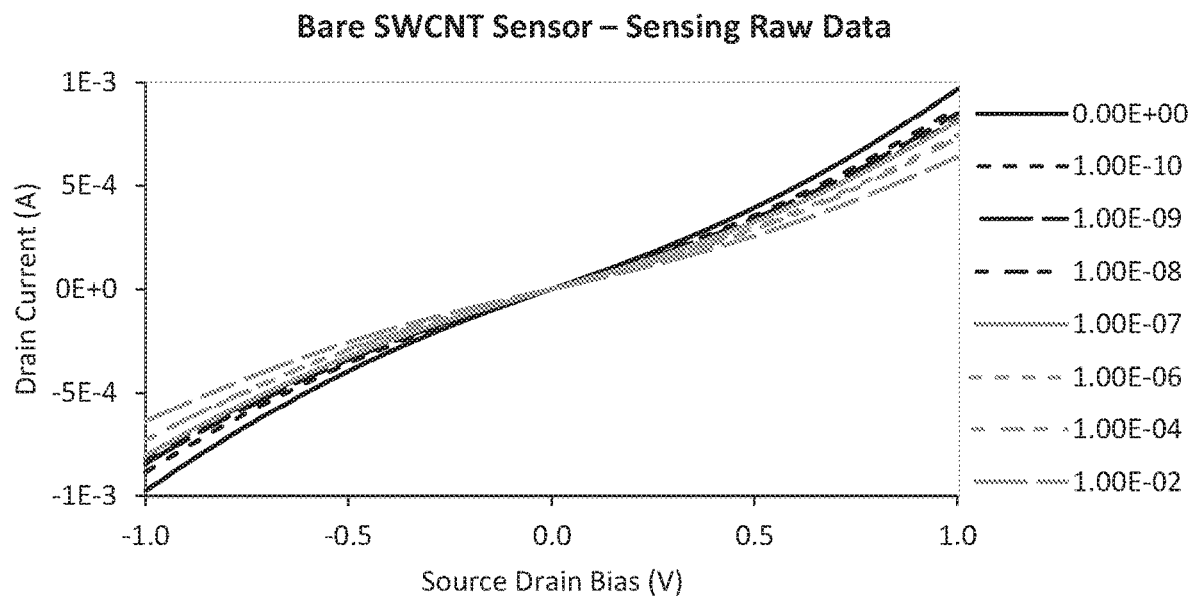
FIG. 7A illustrates the response of a P2 SWCNT chemiresistor sensor hereof to various concentrations of THC when the source-drain bias is swept from −1 to +1 V.
Figure 7B:
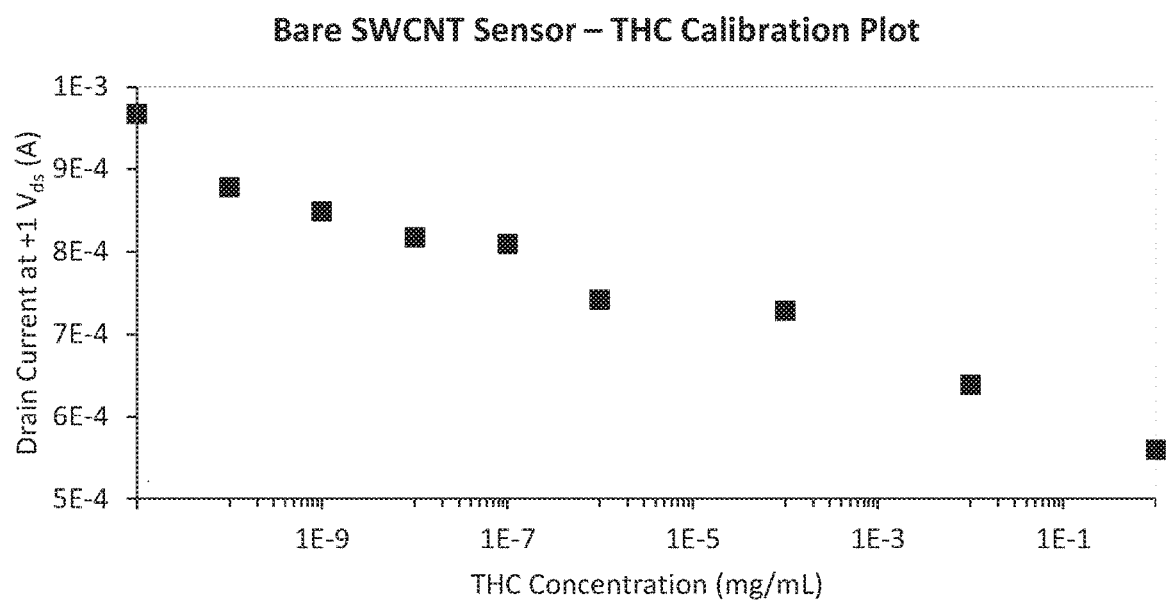
FIG. 7B illustrates that there is a logarithmic relationship between the measured drain current and THC concentration for the sensor of FIG. 7A.

In a number of representative studies, bare SWCNTs were used in simple chemiresistors by sweeping the source-drain bias voltage from −1 to +1. FIG. 7A illustrates the response of a P2 SWCNT chemiresistor sensor hereof to various concentrations of THC when the source-drain bias is swept from −1 to +1. FIG. 7B illustrates that there is a logarithmic relationship between the current and THC concentration for the sensor of FIG. 7A. For THC sensing in a dried state, the selectivity for THC can be improved by evaporating off small molecule cross contaminants, such as ethanol, acetone, and water, that may be present in the breath by, for example, waiting a predetermined period of time and/or heating the microchip. The THC sensors may thus readily be implemented in to a breathalyzer to quantifiably measure THC in someone who is under the influence of marijuana.

Figure 8A:
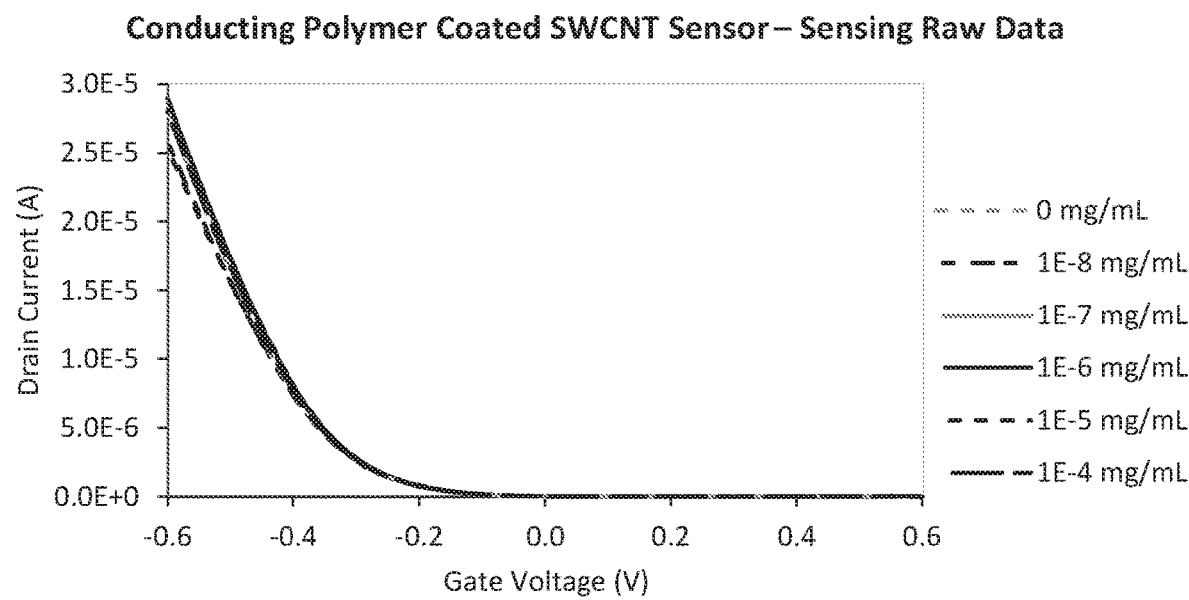
FIG. 8A illustrates results for studies with a IsoSol SWCNT sensor wherein a liquid gate voltage was swept from +0.6 to −0.6 V.
Figure 8B:
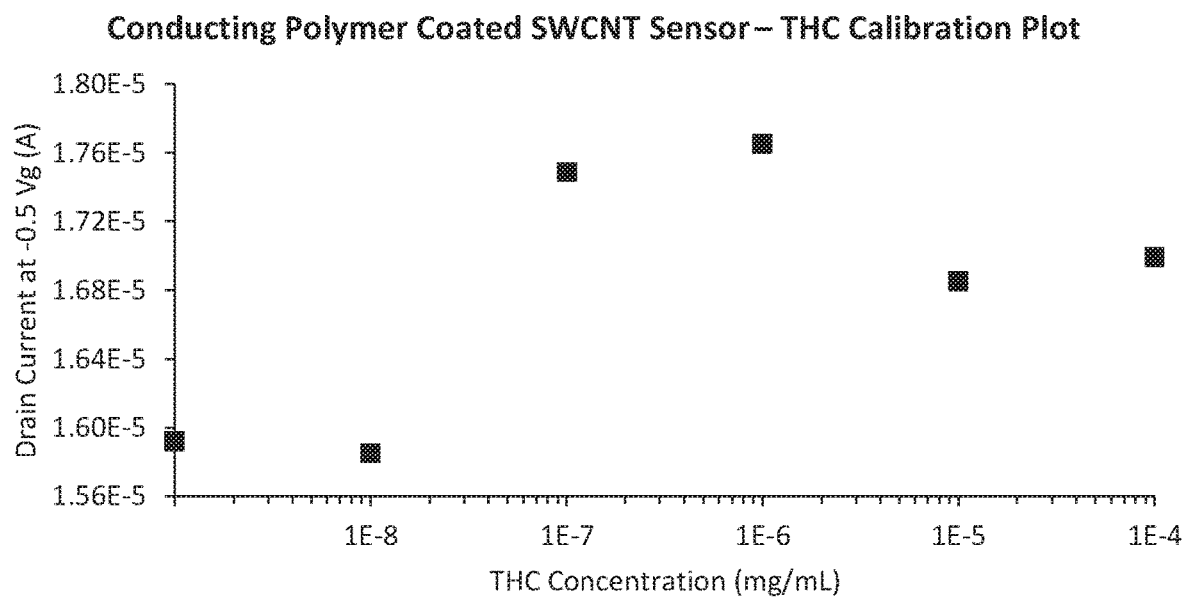
FIG. 8B illustrates that there is no correlation between THC concentration and measured drain current in the sensor of FIG. 8A.

SWCNTs coated with conjugated, conducting polymer (IsoSol SWCNT, coated with a C12 polymer, poly(9,9-di-n-dodecylfluorene)) did not show changes in electrical characteristics that correlated to changes in THC concentration. FIGS. 8A and 8B illustrates results for studies with conductive polymer-coated SWCNTs wherein a gate voltage was swept from +0.6 to −0.6 in a sensor hereof. As illustrated in FIG. 8B, there is no correlation between THC concentration at measured drain current. SWCNTs coated with conducting polymer thus did not show changes in electrical characteristics that correlated to changes in THC concentration. In general, the bare nanostructures or nanostructures decorated or coated with a coating material must interact with THC molecules (for example, receive a donated electron charge from THC) so that a property (for example, an electrical property and/or an optical property) of the sensing medium or material changes in a measurable manner. The degree of interaction between the nanostructure/sensing material may be modified by the choice of the coating around the nanostructures. The effect of various coating materials on the response of nanostructures to THC is readily and quickly determinable as described herein.

Figure 9:
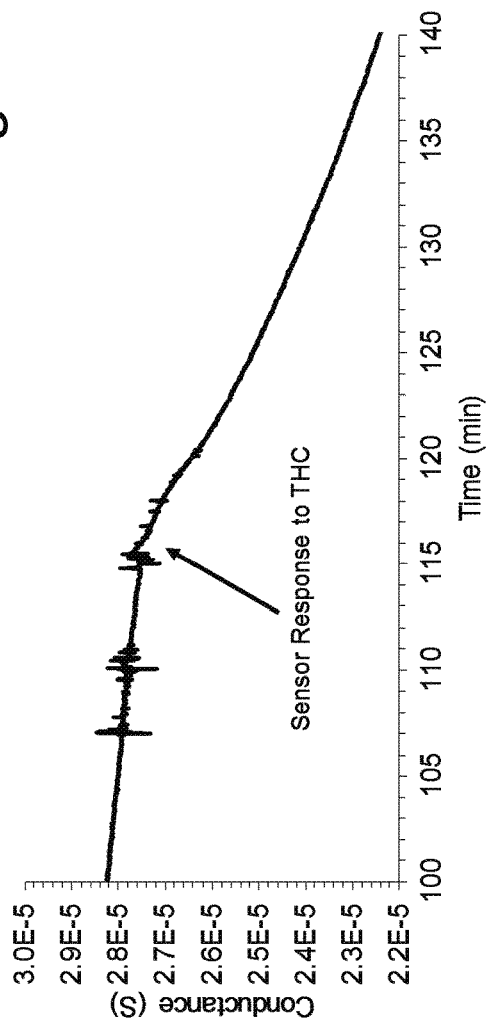
FIG. 9 illustrates the results of a study of a chemiresistor hereof showing THC sensing in a gas phase for IsoSol SWCNT available from Raymor Industries Inc. of Quebec, Canada.

Various types of compositions may be used in the sensing media or materials hereof to provide sensitivity to THC. A number of further studies (described further below) have shown THC sensitivity for Iso-Sol SWCNTs, holey reduced graphene oxide (hrGO) SWCNTs, gold nanoparticle functionalized Iso-Sol SWCNTs and gold nanoparticle functionalized PURUS Nano SWCNTs. Those SWCNTs are purified to high levels of semiconducting enrichment (99.9%) and are coated with TRITON® X-100 surfactant (a nonionic surfactant that has a hydrophilic polyethylene oxide chain (on average it has 9.5 ethylene oxide units) and an aromatic hydrocarbon or hydrophobic group) available from Union Carbide, of Midland, Mich. FIG. 9, for example, illustrates a chemiresistor study showing THC sensing in a gas phase for IsoSol SWCNT. IsoSol SWCNT are commercially available semiconducting enriched SWCNTs with polymer coatings.

Figure 10A:
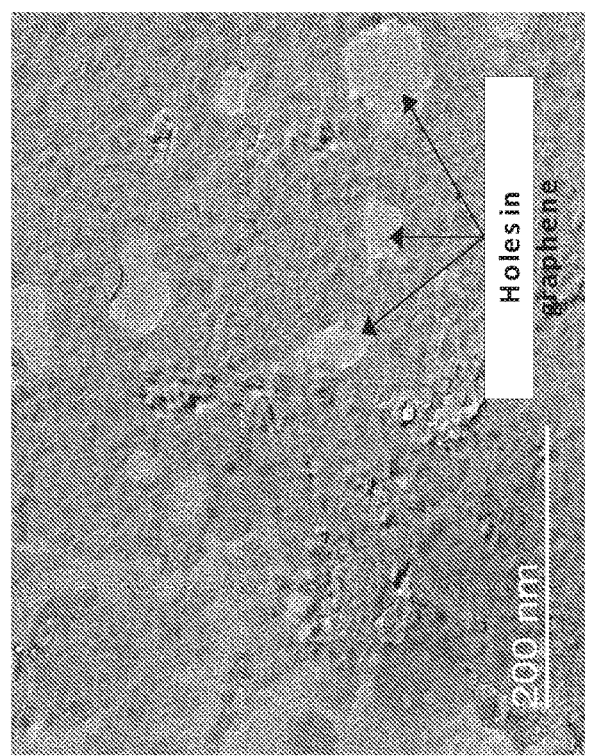
FIG. 10A illustrates a transmission electron microscopy (TEM) image of holey reduced graphene oxide (hrGO).
Figure 10B:
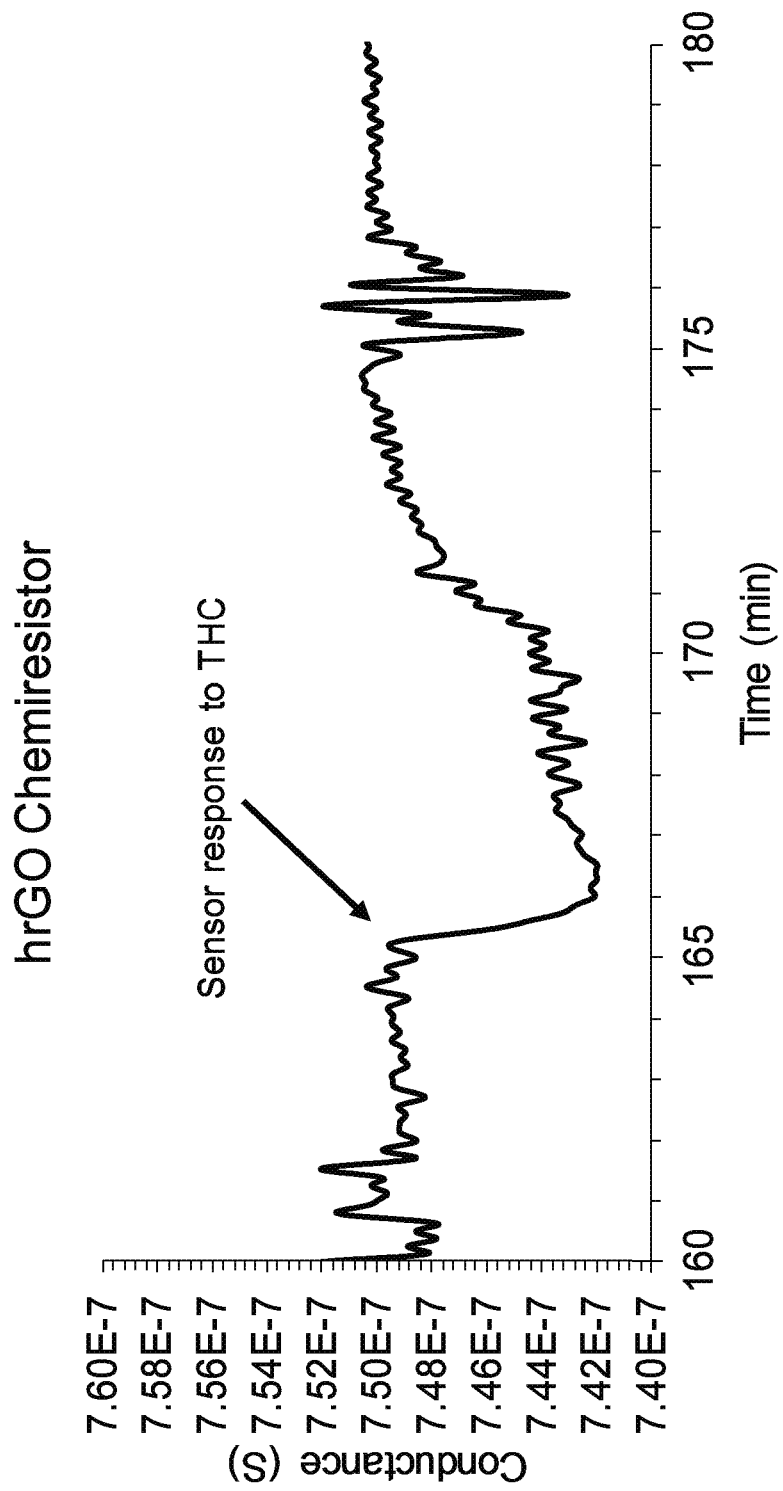
FIG. 10B illustrates THC sensing in a gas phase with a chemiresistor hereof including hrGO.

FIG. 10A illustrates a transmission electron microscopy (TEM) image of holey reduced graphene oxide (hrGO) as, for example, described in U.S. Pat. Nos. 8,920,764 and 9,482,638, the disclosures of which are incorporated herein by reference. Holey reduced graphene oxide may, for example, be produced by oxidation of graphene sheets to form holey graphene oxide sheets having holes in the basal plane thereof, followed by reduction of the holey graphene oxide sheets. The oxidation may, for example, occur enzymatically. The hrGO sheets provide a network of interconnected graphene nanoribbons. FIG. 10B illustrates THC sensing in a gas phase with hrGO.

Figure 11A:
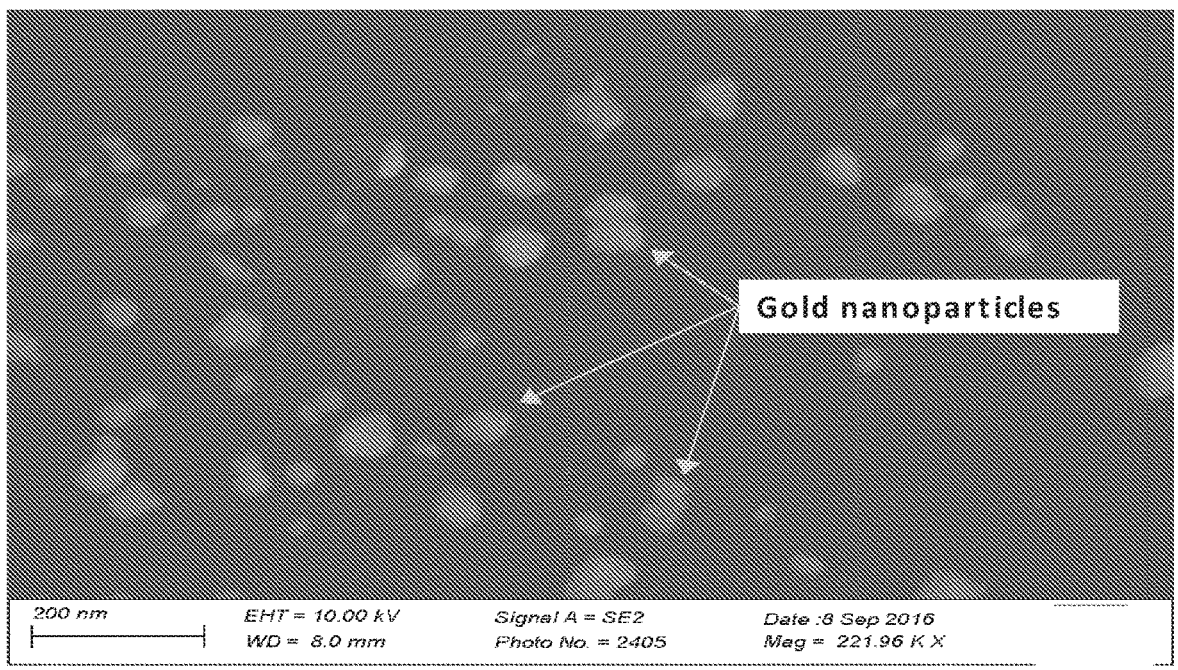
FIG. 11A illustrates a scanning electron microscopy (SEM) raw image of gold particle functionalized PURUS Nano SWCNT.
Figure 11B:
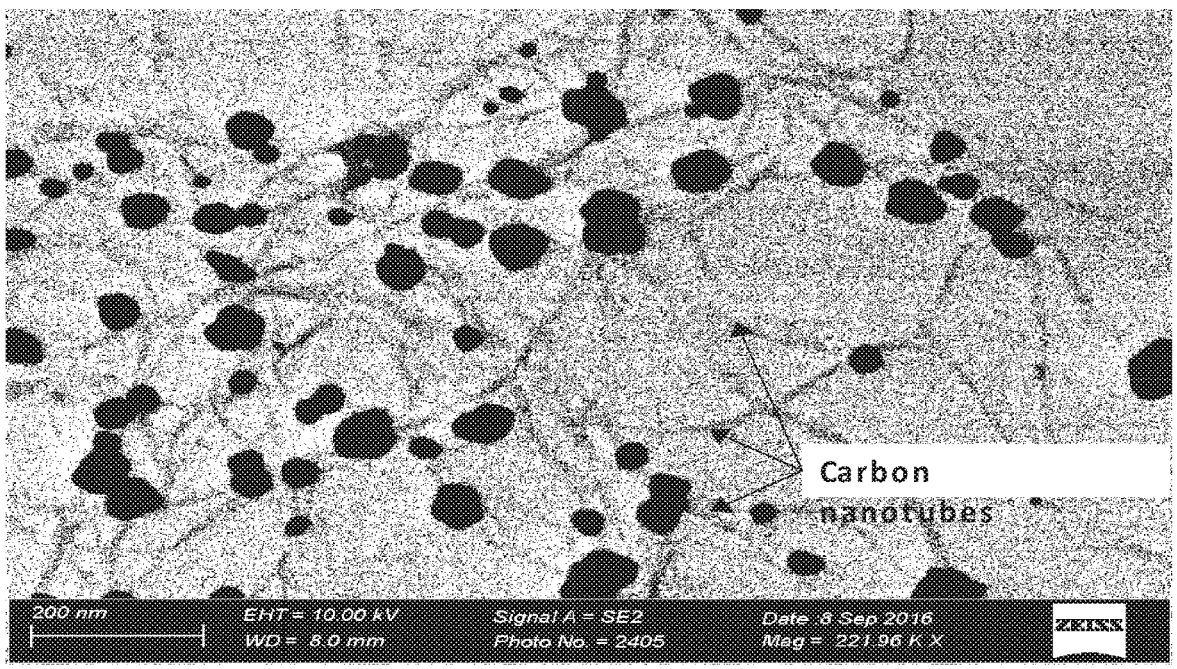
FIG. 11B illustrates a SEM false-colored image of the gold particle functionalized Purus Nano SWCNT of FIG. 11A.
Figure 11C:
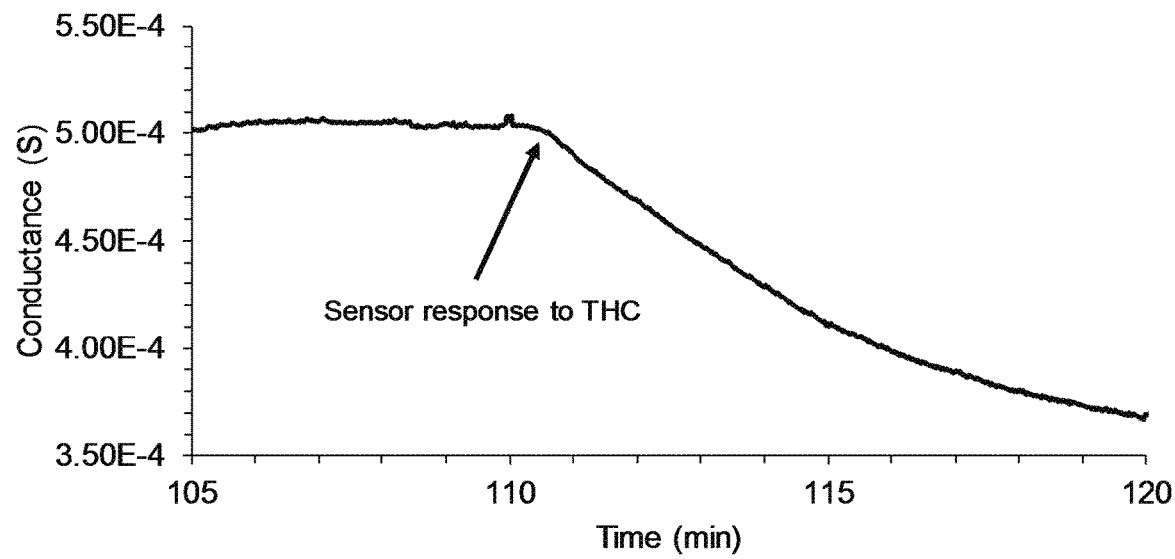
FIG. 11C illustrates THC sensing with the gold particle functionalized Purus Nano SWCNT of FIG. 11A.
Figure 12:
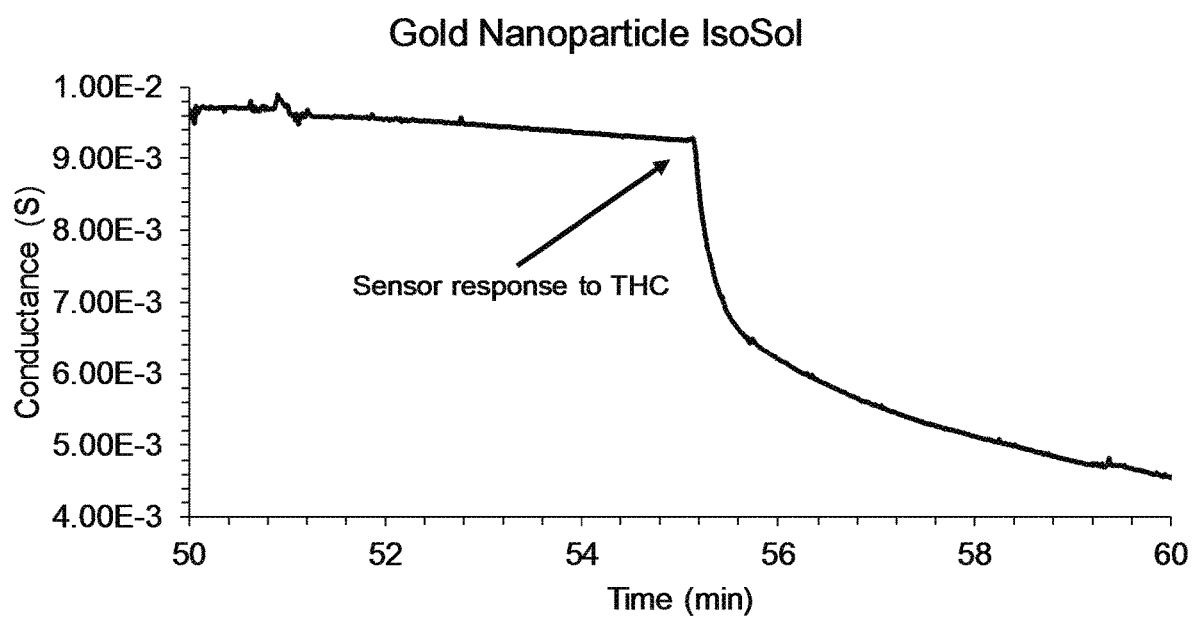
FIG. 12 illustrates THC sensing with gold particle functionalized IsoSol SWCNT.

FIGS. 11A and 11B illustrate, respectively, a scanning electron microscopy or SEM raw image and a false-colored image of gold particle functionalized SWCNT. The semispherical particles in both the raw image of FIG. 11A and the false-colored image of FIG. 11B are gold nanoparticles. The false-colored image was generated to better visualize the carbon nanotubes. FIG. 11C illustrates THC sensing with gold particle functionalized SWCNT available from PURUS Nano in chemiresistor experiments in the gas phase. FIG. 12 illustrates THC sensing with gold particle functionalized IsoSol SWCNT available from Raymore Industries in chemiresistor experiments in the gas phase.

Figure 13A:
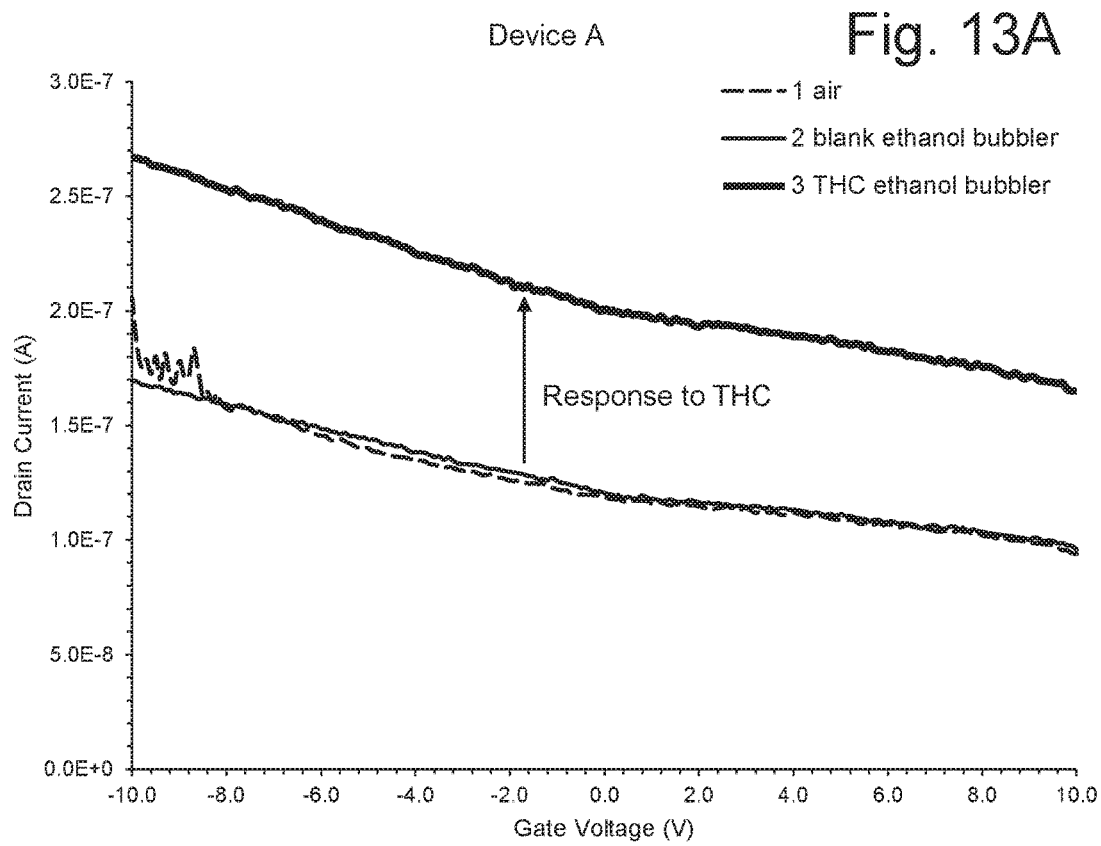
FIG. 13A illustrates output data from a first back-gated field effect transistor or FET device fabricated with Purus Nano SWCNT upon exposure to a combined THC and ethanol vapor stream compared to output data upon exposure to ethanol vapor.
Figure 13B:
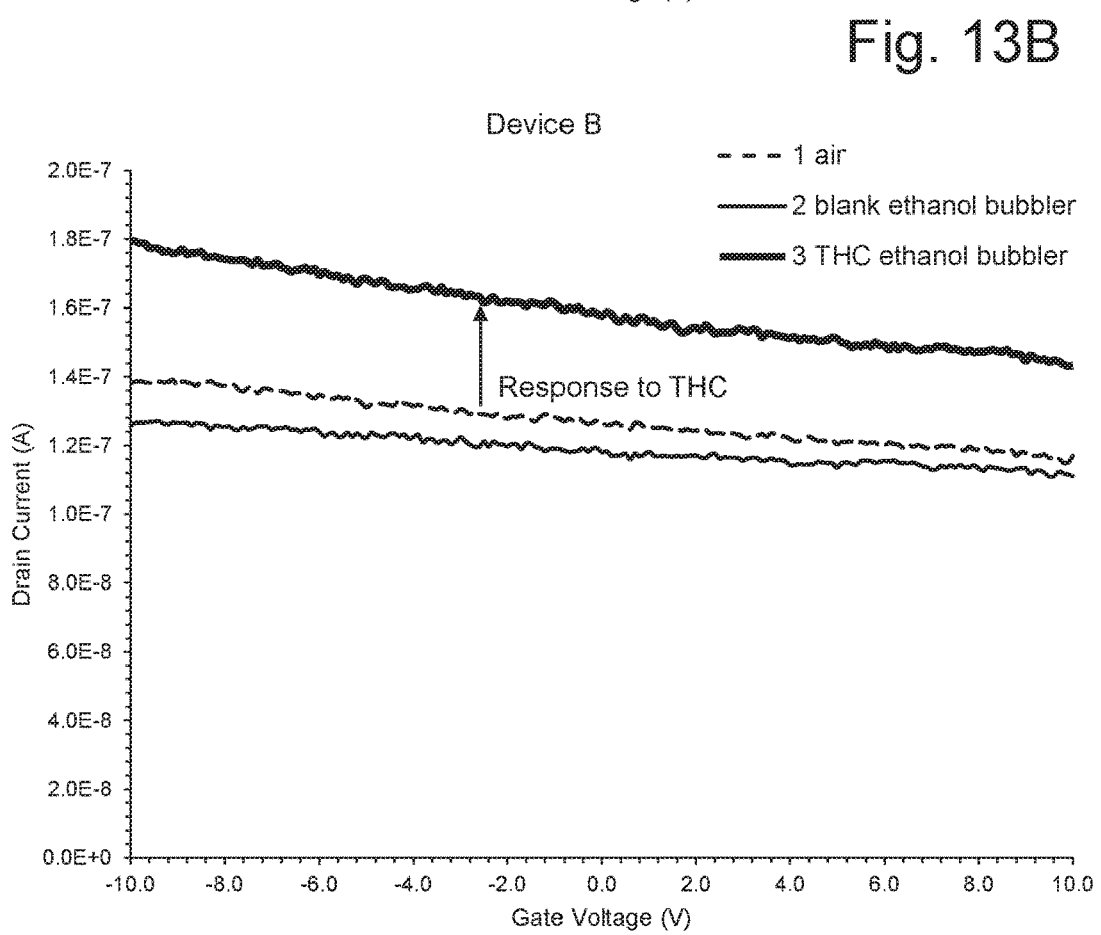
FIG. 13B illustrates output data from a second back-gated FET device fabricated with Purus Nano SWCNT upon exposure to a combined THC and ethanol vapor stream compared to output data upon exposure to ethanol vapor.

FIGS. 13A and 13B illustrate back-gated FET measurements of two sensor devices (Device A and Device B, respectively) fabricated with Purus Nano SWCNT. The devices exhibit larger current changes after exposure to a combined THC and ethanol vapor stream as compared to exposure to pure ethanol vapor or air. In the studies of FIGS. 13A and 13B, the THC and ethanol vapors were generated using a bubbler system. The bubbler system generates vapors by flowing an air stream through a TEFLON (a polytetrafluoroethylene available from The Chemours Company of Wilmington, Del. USA) inlet tubing connected to a sealed bottle. An end of the inlet tubing is immersed in the solution inside the sealed bottle and generates a steady stream of bubbles as air flows in. The other end of the outlet tubing is placed in the head space above the solution, and the other end is placed just above the surface of the sensor chip, delivering any vapor generated directly to the sensor.

Figure 14A:
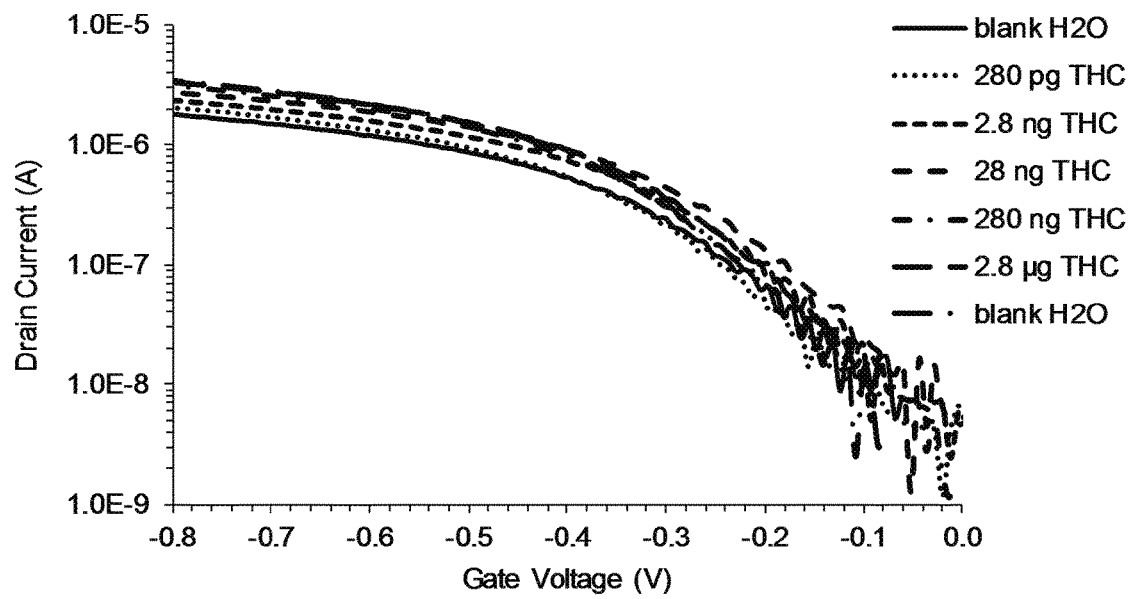
FIG. 14A illustrates data for sensing of THC in liquid water with a FET device hereof including IsoSol SWCNT.
Figure 14B:
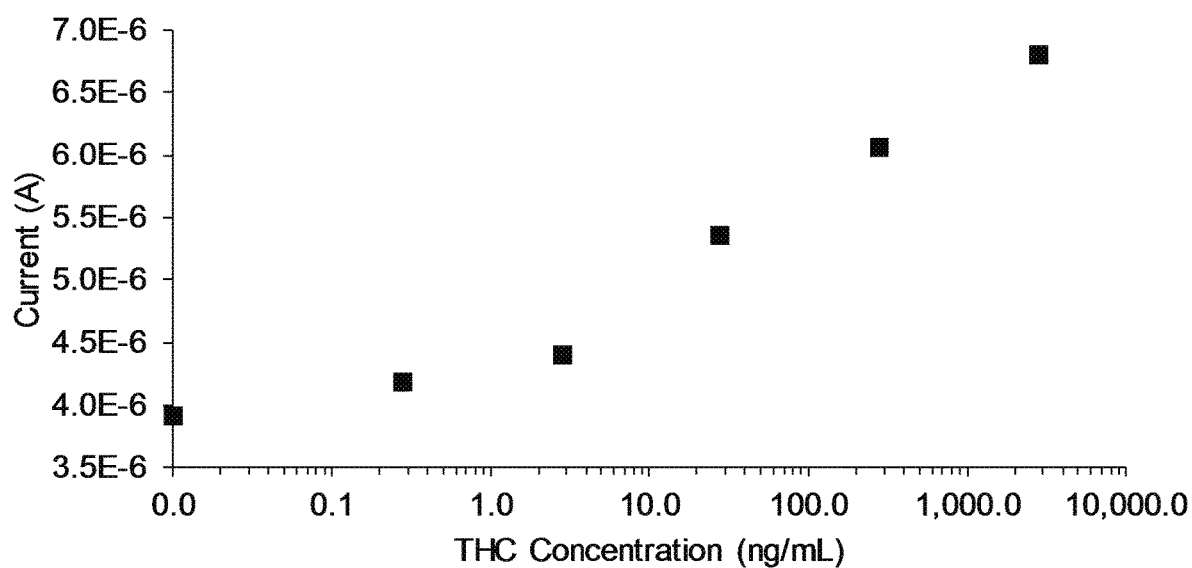
FIG. 14B illustrates a THC calibration curve for the device of FIG. 14A.

As discussed above, FET devices hereof can be used to sense THC in a gas phase or in a liquid phase. FIG. 14A illustrates representative data for sensing of THC in liquid water with a FET device gated with silver-silver chloride (Ag/AgCl) electrode hereof including IsoSol SWCNT. A THC calibration curve for the device of FIG. 14A is illustrated in FIG. 14B which shows logarithmic relationship to concentration from 0 ng/mL up to 2.8 ng/mL with one slope followed by another logarithmic relationship from 2.8 ng/mL to 2.8 μg/mL with a different slope.

Figure 15A:
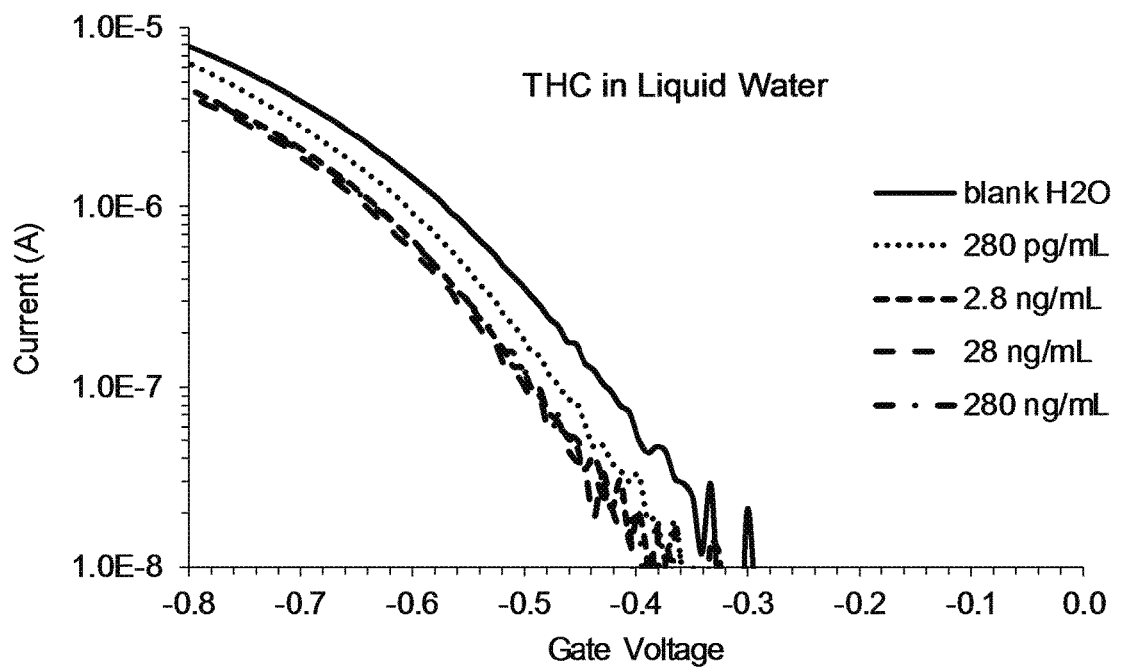
FIG. 15A illustrates data for sensing of THC in liquid water with a FET device hereof including IsoSol conjugated with THC antibodies.
Figure 15B:
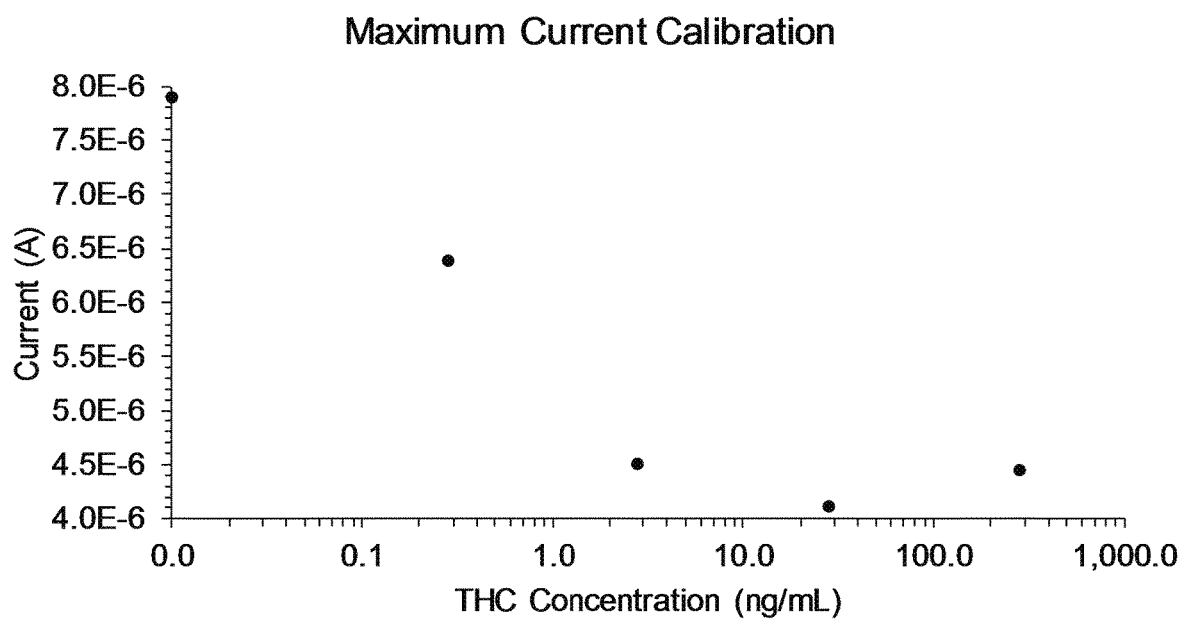
FIG. 15B illustrates a THC calibration curve for the device of FIG. 15A.

FIG. 15A illustrates data for sensing of THC in liquid water with a FET device hereof including IsoSol SWCNT decorated with a biological moiety in the form of THC antibodies. The sensor was incubated with the corresponding concentration of THC for 5 minutes then measured using Ag/AgCl as the gating electrode. FIG. 15B illustrates a THC calibration curve for the device of FIG. 15A showing a logarithmic relationship to concentration up to 2.8 ng/mL followed by antibody binding site saturation above 2.8 ng/mL. The logarithmic relationship does not hold after the antibody sites are saturated. Therefore, the sensor cannot measure concentrations above the saturation threshold.

Figure 16A:
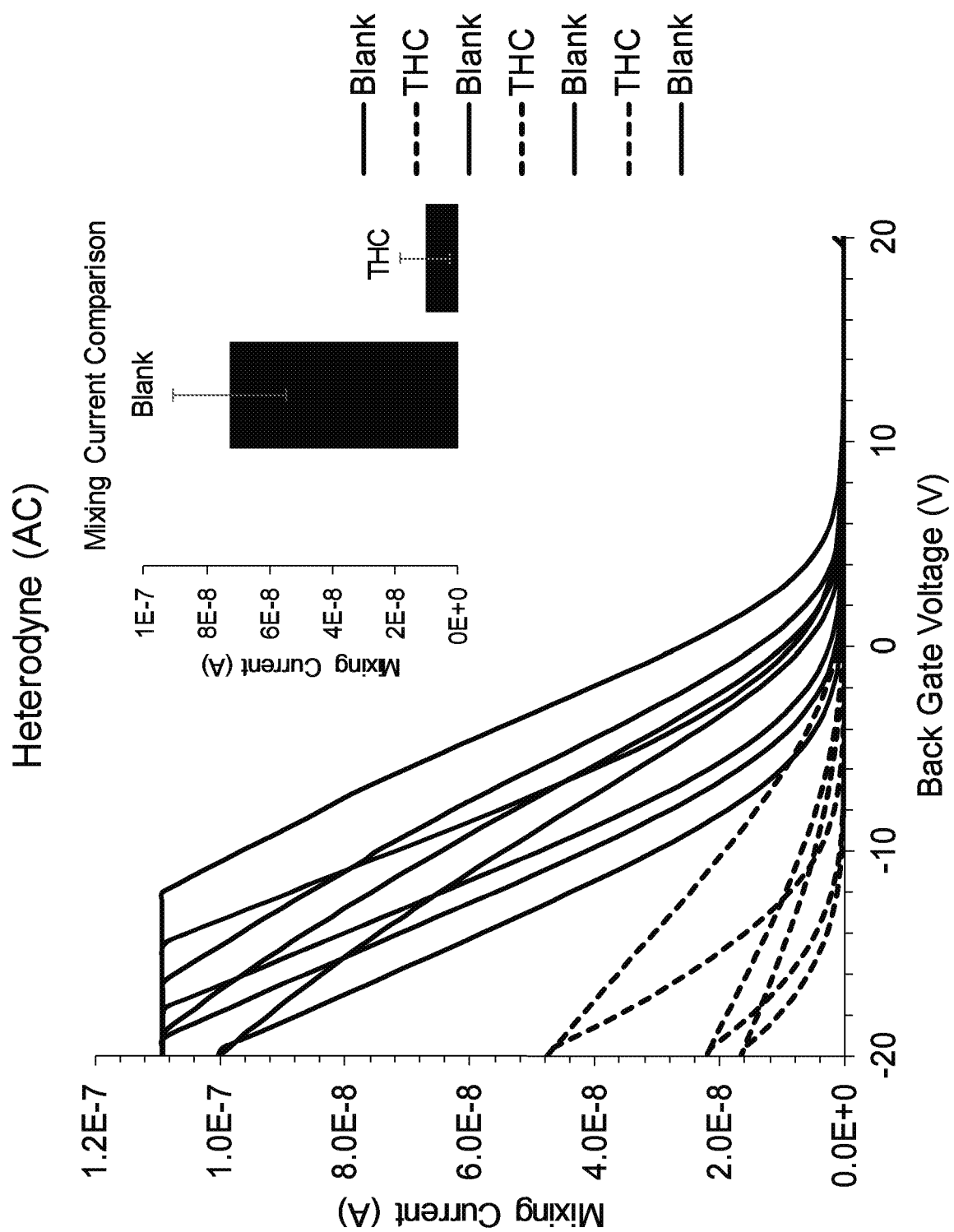
FIG. 16A illustrates data for sensing of THC in solid state with a heterodyne FET device hereof including IsoSol SWCNT wherein THC was deposited on the sensor by depositing THC dissolved ethanol solution on the sensor and evaporating off the volatile ethanol.
Figure 16B:
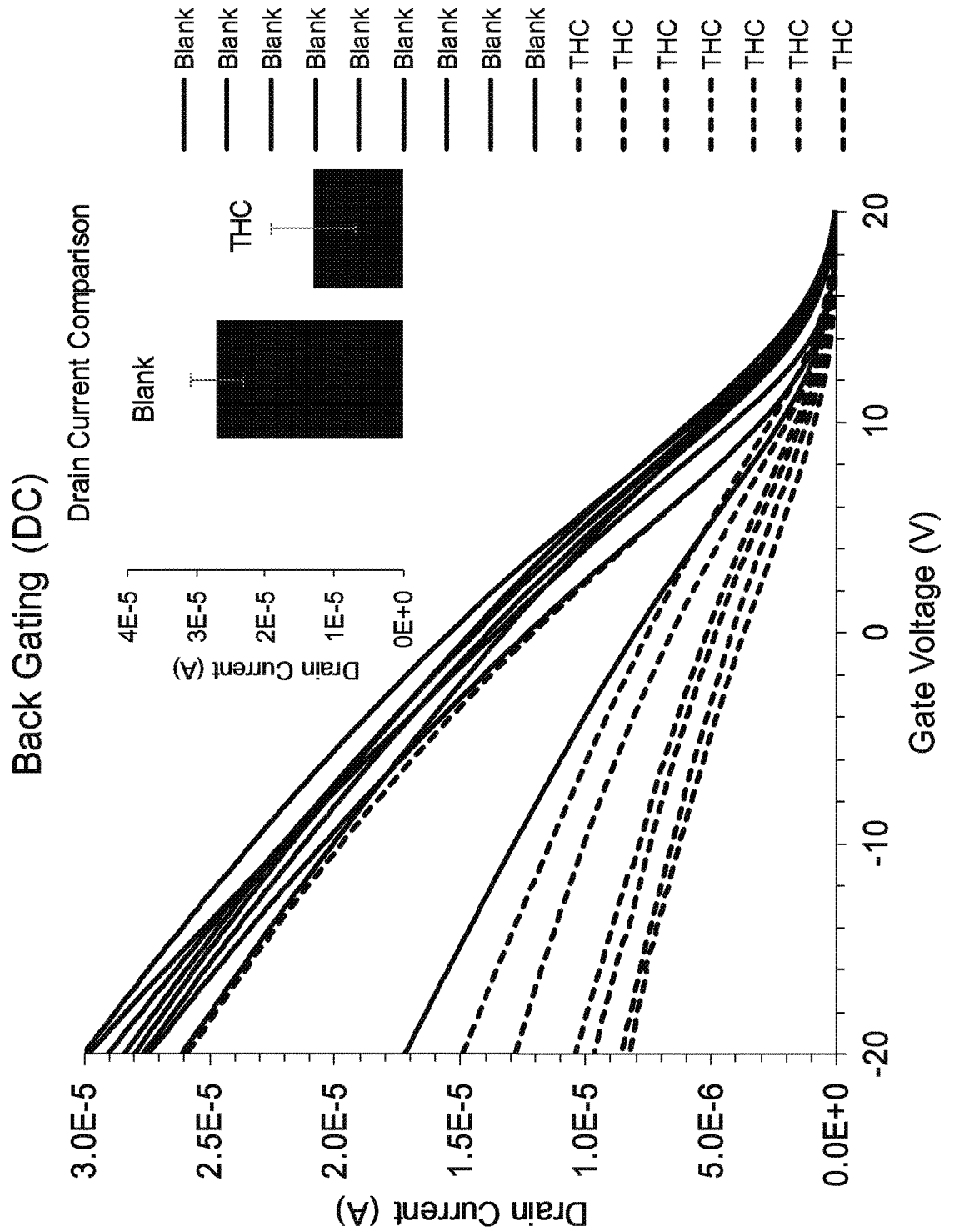
FIG. 16B illustrates data for sensing of THC in solid state with a back gated FET device hereof.

FIG. 16A illustrates representative data for sensing of THC solid state for a heterodyne back gated device hereof including IsoSol SWCNT operated. A heterodyne measurement is a form of an AC measurement that involves enveloping a high frequency (for example, 100 kHz to 10 MHz) sine wave voltage signal in a low frequency (for example, ~1 kHz) sine wave voltage signal using a frequency mixer in the form of a waveform generator. The heterodyne signal enables directly sensing the signal interaction with the dipole moment of molecules at the high frequency, and measurement of the interaction at the low frequency in the form of the mixing current. The mixing current is measured using a lock-in amplifier locked in phase to the heterodyne signal. A Keithely SourceMeter may, for example, be used to back gate the sensor and amplify the measured mixing current. Heterodyne measurements can increase the sensitivity and response times of the sensors. FIG. 16B illustrates representative data for a back gated FET device hereof including IsoSol SWCNT The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A device for detection of a cannabinoid, comprising:
a sensor comprising a substrate and a sensor medium on the substrate, the sensor medium comprising at least one nanostructure, wherein at least one property of the sensor medium is dependent upon the presence of the cannabinoid on a surface of the sensor medium resulting from contacting a breath sample with the surface of the sensor medium to detect the cannabinoid at a concentration present in the breath sample arising from the use of a cannabinoid-containing substance by a person from whom the breath sample is taken; and
electronic circuitry comprising at least one measurement system in operative connection with the sensor to measure a variable relatable to the at least one property of the sensor medium dependent upon the presence of the cannabinoid, wherein the electronic circuitry is configured to delay measurement of the variable for a period of time after contact of the breath sample with the surface of the sensor medium to provide time for evaporation of small-molecule contaminants.

2. The device of claim 1 wherein the sensor is configured to interact with a sample comprising breath.

3. The device of claim 1 further comprising a breathing tube into which breath may be exhaled, an outlet of the breathing tube being in the vicinity of the sensor medium such that breath exhaled into the breathing tube contacts the sensor medium.

4. The device of claim 1 wherein the at least one property of the sensor medium dependent upon the presence of the cannabinoid is an electrical property or an optical property.

5. The device of claim 1 wherein the at least one measurement system is configured to determine a concentration of the cannabinoid based upon a measured value of the variable.

6. The device of claim 5 wherein the sensor further comprises a first conductive terminal in electrical connection with the sensor medium and a second conductive terminal in electrical connection with the sensor medium, the second conductive terminal being spaced from the first conductive terminal.

7. The device of claim 6 wherein the sensor operates as a chemiresistor or a field effect transistor.

8. The device of claim 6 wherein the sensor operates as a chemiresistor.

9. The device of claim 6 wherein the at least one nanostructure is selected from the group consisting of single-walled nanotubes, multiple-wall nanotubes, nanowires, nanofibers, nanorods, nanospheres, and nanoribbons.

10. The device of claim 6 wherein the at least one nanostructure comprises semiconductor enriched single-walled carbon nanotubes.

11. The device of claim 10 wherein the carbon nanostructures comprise at least 99.9% semiconductor enriched single-walled carbon nanotubes.

12. The device of claim 6 wherein the sensor medium comprises a functional material deposited upon the at least one nanostructure.

13. The device of claim 12 wherein the functional material comprises at least one of a polymer, a surfactant, a biological moiety, a metal nanoparticle or a metal oxide nanoparticle.

14. The device of claim 10 wherein the sensor medium comprises a functional material deposited upon the at least one nanostructure.

15. The device of claim 14 wherein the functional material comprises at least one of a polymer, a surfactant, a biological moiety, a metal nanoparticle or a metal oxide nanoparticle.

16. The device of claim 1 wherein the at least one nanostructure comprises carbon, boron, boron nitride, carbon boron nitride, silicon, germanium, gallium nitride, zinc oxide, indium phosphide, molybdenum disulfide or silver.

17. The device of claim 1 wherein the sensor is removable from the device.

18. The device of claim 17 wherein the device comprises a housing comprising a passage therein through which the sensor can be placed in operative connection with the electronic circuitry and removed from operative connection with the electronic circuitry.

19. The device of claim 1 wherein the electronic circuitry is configured to apply at least one of heat or reduced pressure to the sensor during the period of time.

20. The device of claim 1 comprising a plurality of sensors, wherein each of the plurality of sensors comprises a substrate and a sensor medium on the substrate, the sensor medium comprising at least one nanostructure, wherein at least one property of the sensor medium is dependent upon the presence of the cannabinoid on a surface of the sensor medium; and wherein the at least one measurement system is in operative connection with each of the plurality of sensors to measure a variable relatable to the at least one property of the sensor medium of each of the plurality of sensors which is dependent upon the presence of the cannabinoid.

21. The device of claim 1 wherein the cannabinoid is tetrahydrocannabinol or THC.

22. A method of detecting a cannabinoid comprising:
providing a sensor to which a sample of breath is applied to contact a sensor medium of the sensor, the sensor medium being positioned on a substrate of the sensor, the sensor medium comprising at least one nanostructure, wherein at least one property of the sensor medium is dependent upon the presence of the cannabinoid on a surface of the sensor medium; and
subsequent to a delay of a period of time after contact of the breath with the surface of the sensor medium to provide time for evaporation of small-molecule cross contaminants, measuring a variable relatable to the at least one property of the sensor medium which is dependent upon the presence of the cannabinoid to detect the cannabinoid at a concentration present in the sample of breath arising from the use of a cannabinoid-containing substance by a person from whom the sample of breath is taken.

23. The method of claim 22 further comprising having a person exhale such that exhaled breath contacts the sensor medium.

\* \* \* \* \*